US012325743B2

(12) United States Patent
Liu et al.

(10) Patent No.: US 12,325,743 B2
(45) Date of Patent: Jun. 10, 2025

(54) ANTI-TNFα/ANTI IL-17A NATURAL ANTIBODY STRUCTURE-LIKE HETERODIMER FORM OF BISPECIFIC ANTIBODY AND PREPARATION METHOD THEREFOR

(71) Applicant: BEIJING HANMI PHARMACEUTICAL CO., LTD., Beijing (CN)

(72) Inventors: Jiawang Liu, Beijing (CN); Yaping Yang, Beijing (CN); Nanmeng Song, Beijing (CN); Wenchu Xiao, Beijing (CN); Chulwoong Chung, Beijing (CN); Maengsup Kim, Beijing (CN)

(73) Assignee: BEIJING HANMI PHARMACEUTICAL CO., LTD., Beijing (CN)

( * ) Notice: Subject to any disclaimer, the term of this patent is extended or adjusted under 35 U.S.C. 154(b) by 1021 days.

(21) Appl. No.: 17/290,480

(22) PCT Filed: Nov. 5, 2019

(86) PCT No.: PCT/CN2019/115587
§ 371 (c)(1),
(2) Date: Apr. 30, 2021

(87) PCT Pub. No.: WO2020/093990
PCT Pub. Date: May 14, 2020

(65) Prior Publication Data
US 2022/0010006 A1 Jan. 13, 2022

(30) Foreign Application Priority Data
Nov. 5, 2018 (CN) .......................... 201811307673.6

(51) Int. Cl.
*C07K 16/24* (2006.01)
*A61K 39/00* (2006.01)
*C07K 16/46* (2006.01)

(52) U.S. Cl.
CPC .......... *C07K 16/241* (2013.01); *C07K 16/244* (2013.01); *C07K 16/468* (2013.01); *A61K 2039/505* (2013.01); *C07K 2317/31* (2013.01); *C07K 2317/52* (2013.01); *C07K 2317/72* (2013.01); *C07K 2317/76* (2013.01)

(58) Field of Classification Search
CPC .. C07K 16/241; C07K 16/244; C07K 16/468; C07K 2317/31; C07K 2317/52; C07K 2317/72; C07K 2317/76; C07K 14/525; C07K 16/46; C07K 14/54; C07K 2317/55; C07K 2317/622; A61K 2039/505; A61P 17/06; A61P 19/02; A61P 37/00; C12N 15/85
See application file for complete search history.

(56) References Cited

U.S. PATENT DOCUMENTS

| | | | |
|---|---|---|---|
| 11,072,651 B2 * | 7/2021 | Song | A61P 19/02 |
| 2014/0227287 A1 | 8/2014 | Kamohara et al. | |
| 2016/0326241 A1 | 11/2016 | Auer et al. | |
| 2017/0218092 A1 * | 8/2017 | Chiu | A61P 37/00 |

FOREIGN PATENT DOCUMENTS

| | | | |
|---|---|---|---|
| CN | 1215407 A | 4/1999 | |
| CN | 103429620 A | 12/2013 | |
| CN | 103827300 A | 5/2014 | |
| CN | 107556382 A | 1/2018 | |
| JP | 2016510743 A | 4/2016 | |
| KR | 100317188 B1 | 2/2002 | |
| TW | 201444867 A | 12/2014 | |
| WO | 2013/002362 A1 | 1/2013 | |
| WO | 2015014979 A1 | 2/2015 | |
| WO | 2017/132457 A1 | 8/2017 | |
| WO | WO-2018050028 A1 * | 3/2018 | A61K 39/395 |
| WO | 2018059502 A1 | 4/2018 | |
| WO | 2018090950 A1 | 5/2018 | |
| WO | 2018177324 A1 | 10/2018 | |

OTHER PUBLICATIONS

Polyakov et al. (Non)Obviousness of Claims to Genetic Sequences: Finding the Middle Ground, 26 Santa Clara High Tech. L.J. 1 (2009). (Year: 2009).*
Colman P.M., "Effects of Amino Acid Sequence Changes on Antibody-Antigen Interactions", Research in Immunology 145(1):33-36 (1994) (cited and discussed in the Office Action dated Nov. 24, 2021 issued in Russian Application No. 2021114141/10(029974)).
Muller S. et al., "Spliceosomal Peptide P140 for Immunotherapy of Systemic Lupus Erythematosus", Arthritis & Rheumatism 58(12):3873-3883 (Dec. 2008) (cited and discussed in the Office Action dated Nov. 24, 2021 Issued in Russian Application No. 2021114141/10(029974)).
Nedorubov A.A. et al., The Study of Pharmacodynamics of a Medicine Based on Humanized Monoclonal Antibodies Against IL-17 in Rabbit Model of Antigen-Induced Arthritis 16(2):101-107 (2016) (cited and discussed in the Office Action (English-language abstract provided) dated Nov. 24, 2021 issued in Russian Application No. 2021114141/10(029974)).
Qian L. et al., "Advances in Researches on Therapeutic Anti-TNF a Antibodies", Progress in Pharmaceutical Sciences 40(6):437-444 (Jun. 2016) (cited and discussed in the Office Action (English-language abstract provided) dated Jan. 24, 2022 issued in Chinese Application No. 201980071589.5).

(Continued)

*Primary Examiner* — Anand U Desai
*Assistant Examiner* — Amber K Faust
(74) *Attorney, Agent, or Firm* — Scully, Scott, Murphy & Presser, P.C.

(57) ABSTRACT

Provided are an anti-TNFα/anti IL-17A natural antibody structure-like heterodimer form of a bispecific antibody and a preparation method therefor, wherein the antibody can bind two target molecules simultaneously, and can be used for treating complex diseases.

23 Claims, 9 Drawing Sheets
Specification includes a Sequence Listing.

(56) References Cited

OTHER PUBLICATIONS

Safdari Y. et al., "Antibody Humanization Methods—A Review and Update", Biotechnology and Genetic Engineering Reviews 29(2):175-186 (2013) (cited and discussed in the Office Action dated Nov. 24, 2021 issued in Russian Application No. 2021114141/10(029974)).
Torres M. et al., "The Immunoglobulin Constant Region Contributes to Affinity and Specificity", Trends in Immunology 29(2):97-97, 93-94 (2008) (cited and discussed in the Office Action dated Nov. 24, 2021 issued in Russian Application No. 2021114141/10(029974)).
Fan G. et al., "Bispecific Antibodies and Their Applications", Journal of Hematology & Oncology 8(130):1-14 (2015).
Russian Decision to Grant dated Sep. 7, 2022 received in Russian Application No. 2021114141/10, together with an English-language translation.
International Search Report dated Jan. 22, 2020 issued in PCT/CN2019/115587.
Gasser, B., et al., "Antibody production with yeasts and filamentous fungi: on the road to large scale?", Biotechnol Lett (2007) 29:201-212, (cited and discussed in the Office Action dated Feb. 21, 2022 issued in Russian Application No. 2021114141/10(029974)).
Second Office Action dated Sep. 19, 2024, received in Korean Application No. 10-2021-7016468, 12 pages.

\* cited by examiner

A

B

A

B

SEQUENCE LISTING

```
<160> NUMBER OF SEQ ID NOS: 19

<210> SEQ ID NO 1
<211> LENGTH: 321
<212> TYPE: DNA
<213> ORGANISM: artificial
<220> FEATURE:
<223> OTHER INFORMATION: anti-human TNFalpha antibody light chain
      variable region

<400> SEQUENCE: 1
gacatccaga tgacccaatc cccttcctcc ctcagcgcga gcgtcggaga cagggtgaca      60
atcacctgca gggcctccca gggaatccgg aactatctcg cctggtatca gcagaagccc     120
```

```
ggcaaggccc ccaagctgct gatctacgct gccagcacac tccaatccgg cgtgccttcc    180
aggttctccg gaagcggatc cggcaccgac ttcaccctca ccatttccag cctgcagccc    240
gaagacgtcg ccacctacta ctgccagcgg tacaacaggg cccctacac cttcggccaa    300 ggcaccaagg tcgagatcaa g                                              321
```

<210> SEQ ID NO 2
<211> LENGTH: 107
<212> TYPE: PRT
<213> ORGANISM: artificial
<220> FEATURE:
<223> OTHER INFORMATION: anti-human TNFalpha antibody light chain
      variable region

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

<210> SEQ ID NO 3
<211> LENGTH: 321
<212> TYPE: DNA
<213> ORGANISM: artificial
<220> FEATURE:
<223> OTHER INFORMATION: anti-human TNFalpha antibody light chain
      constant region

<400> SEQUENCE: 3

```
aggaccgtgg ccgcccccag cgtgttcatc ttccctccct ccgacgagca gctgaagagc    60
ggcacagcca gcgtcgtgtg cctgctcaac aacttctacc ccagggaagc caaggtgcag    120
tggaaggtgg acaacgccct gcagtccggc aacagccagg agagcgtgac cgaacaggac    180
agcaaggaca gcacctacag cctgagctcc accctcaccc tgtccaaggc cgactacgag    240
aagcataagg tgtacgcctg cgaagtgacc atcagggcc tgtccagccc cgtgacaaag    300
tccttcaaca ggggcgaatg c                                              321
```

<210> SEQ ID NO 4
<211> LENGTH: 107
<212> TYPE: PRT
<213> ORGANISM: artificial
<220> FEATURE:
<223> OTHER INFORMATION: anti-human TNFalpha antibody light chain
      constant region

<400> SEQUENCE: 4

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
                20                  25                  30
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 363
<212> TYPE: DNA
<213> ORGANISM: artificial
<220> FEATURE:
<223> OTHER INFORMATION: anti-human TNFalpha antibody heavy chain
      variable region

<400> SEQUENCE: 5
gaggtgcagc tggtggaatc cggaggagga ctggtccaac tggcaggtc cctcaggctc      60 tcctgtgctg ccagcggctt taccttcgac gattacgcta tgcattgggt gcggcaagcc    120
cctggcaaag gactgaatgg gtgagcgcc attacctgga actccggcca catcgactac     180
gccgactccg tggagggccg gtttaccatt agccgggaca acgccaagaa ctccctgtac    240
ctgcagatga acagcctgag ggctgaggac accgctgtgt actactgcgc caaggtgagc    300
tacctgtcca cagccagcag cctggattac tggggccagg gcaccctggt gacagtcagc    360
agc                                                                  363

<210> SEQ ID NO 6
<211> LENGTH: 121
<212> TYPE: PRT
<213> ORGANISM: artificial
<220> FEATURE:
<223> OTHER INFORMATION: anti-human TNFalpha antibody heavy chain
      variable region

<400> SEQUENCE: 6

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 7
```

```
<211> LENGTH: 990
<212> TYPE: DNA
<213> ORGANISM: artificial
<220> FEATURE:
<223> OTHER INFORMATION: anti-human TNFalpha antibody heavy chain
      constant region

<400> SEQUENCE: 7
gctagcacaa aaggaccttc cgtgtttcca ctggcaccct ctagtaagag tacttcagga      60
ggaaccgcag cactgggatg tctggtgaag gactacttcc cagagcccgt caccgtgtct    120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaaccc    300
aagtcctgcg ataagaccca cacatgccct cctgtcctg ctcccgaact gctgggagga    360
ccctccgtct tcctgttccc ccccaagccc aaagacacac tgatgatcag caggacccct    420
gaagtgacct gcgtggtcgt ggacgtgagc acgaggacc ccgaggtcaa gtttaactgg    480
tacgtggacg gcgtggaggt ccacaacgcc aagaccaagc cagggagga gcagtacaac    540
agcacctaca gggtcgtgtc cgtgctgacc gtgctccacc aagattggct caacggcaag    600
gagtataagt gcaaagtcag caacaaggcc ctccccgccc ccatcgagaa aaccatcagc    660
aaggccaagg gccaaccgcg ggaacctcaa gtgtataccc tccctcccag ccggatgag    720
ctgaccaaga accaagtctc cctcttgtgc ctggtcaagg gattctaccc ttccgacatt    780
gccgtcgaat gggagagcaa tggccagccc gagaacaact acaagacaac ccccccgtc    840
ctgcgcagcg acggatcctt cttcctgtac tccaagctca ccgtggacaa gagccggtgg    900
caacagggca acgtgttctc ctgtagcgtg atgcacgaag ccctccacaa ccactatacc    960
cagaagagcc tgagcctcag ccccggcaaa                                    990

<210> SEQ ID NO 8
<211> LENGTH: 330
<212> TYPE: PRT
<213> ORGANISM: artificial
<220> FEATURE:
<223> OTHER INFORMATION: anti-human TNFalpha antibody heavy chain
      constant region

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Arg Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 333
<212> TYPE: DNA
<213> ORGANISM: artificial
<220> FEATURE:
<223> OTHER INFORMATION: anti-human IL-17 antibody light chain variable
      region

<400> SEQUENCE: 9
atcatcgtca tgacccagtc cccctgtcc ctgcctgtga cactgggcca gcctgcctcc      60
atctcctgca ggtcctccca gagcctggtg cacagcaacg gcaacaccta cctgcactgg   120
tatcaacaga ggcctggcca gagccctagg ctgctgatct acaaggtgta caaccggttc   180
tccggcgtgc ctgacaggtt ctccggcagc ggttctggca ccgacttcac cctgaagatc   240
tccagggtgg aggccgagga tgtgggcgtg tacttctgca gccagtccac ccacttccct   300
accttcggcc agggcaccag gctggagatc aag                                333

<210> SEQ ID NO 10
<211> LENGTH: 111
<212> TYPE: PRT
<213> ORGANISM: artificial
<220> FEATURE:
<223> OTHER INFORMATION: anti-human IL-17 antibody light chain variable
      region

<400> SEQUENCE: 10

Ile Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
```

35                  40                  45
Pro Arg Leu Leu Ile Tyr Lys Val Tyr Asn Arg Phe Ser Gly Val Pro
                50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro Thr Phe Gly Gln Gly Thr Arg Leu Glu Ile Lys
                100                 105                 110

<210> SEQ ID NO 11
<211> LENGTH: 360
<212> TYPE: DNA
<213> ORGANISM: artificial
<220> FEATURE:
<223> OTHER INFORMATION: anti-human IL-17 antibody heavy chain variable
      region

<400> SEQUENCE: 11
caggtgcagg tgcaggaatc cggccctgga ctggtgaagc cctccgagac cctgtccctg    60
acctgtaccg tgtccggcaa ctccatcacc tcctactacg cctggaactg gatcaggcag   120
cctcccggaa agggcctgga gtggatgggc tacatcacct actccggcac cacctcctac   180 aaccctccc tgaagagccg gatcaccatc agcgtggaca cctccaagaa ccagttctcc   240
ctgaaactgt cctccgtgac agccgccgat accgccgtgt actactgcgc ccggggagag   300
tacgacgaca tctacgccgt ggactactgg ggccagggca cactggtgac cgtgtcctcc   360

<210> SEQ ID NO 12
<211> LENGTH: 120
<212> TYPE: PRT
<213> ORGANISM: artificial
<220> FEATURE:
<223> OTHER INFORMATION: anti-human IL-17 antibody heavy chain variable
      region

<400> SEQUENCE: 12

Gln Val Gln Val Gln Glu Ser Gly Pro Gly Leu Val Lys Pro Ser Glu
1               5                   10                  15

Thr Leu Ser Leu Thr Cys Thr Val Ser Gly Asn Ser Ile Thr Ser Tyr
                20                  25                  30

Tyr Ala Trp Asn Trp Ile Arg Gln Pro Pro Gly Lys Gly Leu Glu Trp
            35                  40                  45

Met Gly Tyr Ile Thr Tyr Ser Gly Thr Thr Ser Tyr Asn Pro Ser Leu
        50                  55                  60

Lys Ser Arg Ile Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Glu Tyr Asp Asp Ile Tyr Ala Val Asp Tyr Trp Gly Gln
                100                 105                 110

Gly Thr Leu Val Thr Val Ser Ser
        115                 120

<210> SEQ ID NO 13
<211> LENGTH: 990
<212> TYPE: DNA
<213> ORGANISM: artificial
<220> FEATURE:
<223> OTHER INFORMATION: anti-human IL-17 antibody heavy chain constant region

<400> SEQUENCE: 13

```
gctagcacaa aaggaccttc cgtgtttcca ctggcaccct ctagtaagag tacttcagga      60
ggaaccgcag cactgggatg tctggtgaag gactacttcc cagagcccgt caccgtgtct     120
tggaacagtg gagcactgac ctccggggtc catacatttc ctgccgtgct gcagtcatcc     180
ggtctgtata gcctgagctc tgtggtcaca gtcccaagtt catccctggg cacccagaca     240
tacatctgca acgtgaatca caaaccttcc aatactaagg tcgacaagaa agtggaaccc     300
aagtcctgcg ataagaccca cacatgcccc cttgtcctg ccctgaact gctcggaggc       360
cctagcgtgt tcctcttccc tcccaaaccc aaggacaccc tcatgatctc caggacccct    420
gaggtgacct gcgtcgtggt ggacgtcagc cacgaggacc ccgaggtgaa gttcaactgg    480
tacgtggacg gcgtcgaggt ccacaacgcc aagacaaagc ccgggagga acagtacaac     540
agcacctaca gggtggtcag cgtgctgacc gtgctgcacc aggattggct caacggcaag    600
gagtacaagt gcaaagtctc caacaaggcc ctgcccgccc catcgagaa gaccatctcc    660
aaggctaagg gacagcccag ggagcccaa gtgtacaccg agcctcccag ccgggatgag     720
ctgaccaaga ccaagtctc cctcacctgc ctggtcaagg gattctaccc ttccgacatt     780
gccgtcgaat gggagagcaa tggccagccc gagaacaact acaagacaac ccccccccgtc   840
ctggatagcg acggatcctt cttcctgctc tccgtgctca ccgtcgacaa gagcagatgg    900
cagcagggca acgtgttcag ctgtagcgtg atgcacgagg ccctgcacaa ccactacacc    960
cagaagagcc tgtccctcag ccccggcaag                                      990
```

<210> SEQ ID NO 14
<211> LENGTH: 330
<212> TYPE: PRT
<213> ORGANISM: artificial
<220> FEATURE:
<223> OTHER INFORMATION: anti-human IL-17 antibody heavy chain constant region

<400> SEQUENCE: 14

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Glu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Leu Ser Val Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 321
<212> TYPE: DNA
<213> ORGANISM: artificial
<220> FEATURE:
<223> OTHER INFORMATION: Anti-mouse IL-17A antibody light chain variable
      region

<400> SEQUENCE: 15
gacatccaga tgacacagtc ccccagcttc ctgagcgcta gcgtgggaga gagggtgacc      60
ctgagctgca aggccagcca gaacatcaac aagtacctgg actggttcca gcagaagctg     120
ggcgaagccc ccaagctgct gatctacaac gccgacaacc tccataccgg cattcccagc     180
aggttcagcg gctccggctc cttcagcgac ttcatcctga ccatcagcag cctgcagccc     240
gaggatgacg ccacctactt ctgcctgcag agggaatcct ggccttacac cttcggcgcc     300
ggcaccaagc tggaactgaa g                                               321

<210> SEQ ID NO 16
<211> LENGTH: 107
<212> TYPE: PRT
<213> ORGANISM: artificial
<220> FEATURE:
<223> OTHER INFORMATION: Anti-mouse IL-17A antibody light chain variable
      region

<400> SEQUENCE: 16

Asp Ile Gln Met Thr Gln Ser Pro Ser Phe Leu Ser Ala Ser Val Gly
1               5                   10                  15

Glu Arg Val Thr Leu Ser Cys Lys Ala Ser Gln Asn Ile Asn Lys Tyr
            20                  25                  30

Leu Asp Trp Phe Gln Gln Lys Leu Gly Glu Ala Pro Lys Leu Leu Ile
        35                  40                  45

Tyr Asn Ala Asp Asn Leu His Thr Gly Ile Pro Ser Arg Phe Ser Gly
    50                  55                  60
```

```
Ser Gly Ser Phe Ser Asp Phe Ile Leu Thr Ile Ser Ser Leu Gln Pro
 65                  70                  75                  80

Glu Asp Asp Ala Thr Tyr Phe Cys Leu Gln Arg Glu Ser Trp Pro Tyr
                 85                  90                  95

Thr Phe Gly Ala Gly Thr Lys Leu Glu Leu Lys
            100                 105
```

<210> SEQ ID NO 17
<211> LENGTH: 366
<212> TYPE: DNA
<213> ORGANISM: artificial
<220> FEATURE:
<223> OTHER INFORMATION: Anti-mouse IL-17A antibody heavy chain variable
      region

<400> SEQUENCE: 17

```
caggtgcaac tgaaggagag cggccccgga ctggtgcaac cttcccaaac actcagcctc      60
acctgtaccg tctccggatt ctccctgacc aactattacg tccactgggt cagacagcct    120
cccggcaagg gactggagtg gatgggaggc gtgtggaatg acggcgacac ctcctacaac    180
agcgtcctca ggagcagact gagcattacc agagacacca gcaagagcca ggtcctcctc    240
aagatgtcct cctccagac agaagacacc gccacctatt actgcgccag ggaaggcagg    300
gaaggcttcg tcggctacta tgtgatggat gcttggggcc ctggagctag cgtgacagtg    360
agctcc                                                              366
```

<210> SEQ ID NO 18
<211> LENGTH: 122
<212> TYPE: PRT
<213> ORGANISM: artificial
<220> FEATURE:
<223> OTHER INFORMATION: Anti-mouse IL-17A antibody heavy chain variable
      region

<400> SEQUENCE: 18

```
Gln Val Gln Leu Lys Glu Ser Gly Pro Gly Leu Val Gln Pro Ser Gln
 1               5                  10                  15

Thr Leu Ser Leu Thr Cys Thr Val Ser Gly Phe Ser Leu Thr Asn Tyr
             20                  25                  30

Tyr Val His Trp Val Arg Gln Pro Pro Gly Lys Gly Leu Glu Trp Met
             35                  40                  45

Gly Gly Val Trp Asn Asp Gly Asp Thr Ser Tyr Asn Ser Val Leu Arg
     50                  55                  60

Ser Arg Leu Ser Ile Thr Arg Asp Thr Ser Lys Ser Gln Val Leu Leu
 65                  70                  75                  80

Lys Met Ser Ser Leu Gln Thr Glu Asp Thr Ala Thr Tyr Tyr Cys Ala
                 85                  90                  95

Arg Glu Gly Arg Glu Gly Phe Val Gly Tyr Tyr Val Met Asp Ala Trp
            100                 105                 110

Gly Pro Gly Ala Ser Val Thr Val Ser Ser
            115                 120
```

<210> SEQ ID NO 19
<211> LENGTH: 15
<212> TYPE: PRT
<213> ORGANISM: artificial
<220> FEATURE:
<223> OTHER INFORMATION: GPI325-339

<400> SEQUENCE: 19

-continued

```
Ile Trp Tyr Ile Asn Cys Phe Gly Cys Glu Thr His Ala Met Leu
1               5                   10                  15
```

ANTI-TNFα/ANTI IL-17A NATURAL ANTIBODY STRUCTURE-LIKE HETERODIMER FORM OF BISPECIFIC ANTIBODY AND PREPARATION METHOD THEREFOR

FIELD OF THE INVENTION

The present invention relates to an anti-TNFα/anti-IL-17A natural antibody structure-like heterodimeric bispecific antibody, and a preparation method thereof. Specifically, the invention provides a highly stable heterodimeric anti-TNFα/anti-IL-17A bispecific antibody having the characteristics of a natural IgG and having no mismatched heavy and light chains, and a method of preparing the same.

INCORPORATION BY REFERENCE OF SEQUENCE LISTING

The Sequence Listing in an ASCII text file, named as 39481_Sequence_Listing.txt of 21 KB, created on Apr. 29, 2021, and submitted to the United States Patent and Trademark Office via EFS-Web, is incorporated herein by reference.

BACKGROUND

TNFα is an inflammatory cytokine that induces secretion of other inflammatory factors by binding to its receptors TNFR1 and TNFR2. The antagonists of TNFα can prevent such a binding so as to decrease the activities of the TNFα signal pathway in purpose of inhibiting inflammatory reactions. The antagonists of TNFα currently marketed mainly comprise soluble TNFα receptors and monoclonal anti-TNFα antibodies. A soluble TNFα receptor is prepared by fusing an extracellular region of TNFR2 with a constant region of an IgG, such as Etanercept marketed by Pfizer Pharmaceutical Ltd. in 1998. A monoclonal anti-TNFα a antibody is a genetically engineered antibody that specifically recognizes TNFα, and is capable of neutralizing TNFα, wherein Infliximab and Golimumab from Johnson & Johnson Pharmaceuticals Ltd., Certolizumab from UCB Pharma S.A., and Adalimumab from Abbott Laboratories Ltd. (Clinical Immunology, 2008, 126: 13-30) are currently marketed. Clinical applications show that antagonists of TNFα can effectively alleviate RA inflammation and relieve radiological progression of joints, and the improvement rate of the ACR20 index of patients reaches up to 50-70%. However, it has also been found that 20-30% of patients respond poorly to antagonists of TNFα or the effects decline gradually after having subjected to a long-term treatment of antagonists of TNFα (Biodrugs, 2009, 23 (2): 111-124).

Recent studies have found that Th17 cell levels and IL-17A cytokine expression levels are elevated in RA patients who respond poorly, or whose treatment effects gradually failed after treatment. This phenomenon has also been found in animal models where Th17 cell levels and IL-17A cytokine expression levels are elevated in animals that respond poorly to antagonists of TNFα. A number of documents have reported that IL-17A can synergistically act with TNFα to induce or exacerbate inflammatory responses, and that elevated Th17 and IL-17A in the body might be the important mechanisms for the unsatisfactory antagonist response of TNFα (Trends Pharmacol Sci. 2015 April; 36 (4): 189-95. Ann Rheum Dis. 2012 October; 71 (10): 1741-8. PLoS ONE 2014, 9 (5): e 95346.). It is therefore reasonable to believe that co-inhibition of TNFα and IL-17A may lead to better treatment of RA patients and those subjecting to other TNFα- and IL-17A related autoimmune diseases such as psoriasis, psoriatic arthritis, and lead to an improved quality of life.

In view of this, there is a need to develop a novel therapeutic agent capable of simultaneously blocking TNFα and IL-17A signaling pathways.

SUMMARY OF THE INVENTION

The invention provides a novel and highly stable heterodimeric bifunctional antibody which has the structural characteristics of a natural IgG and has no mismatched heavy and light chains, and is capable of simultaneously blocking TNFα and IL-17A, and a method of preparing the same. The bifunctional antibody tends to selectively bind to tumor cells that simultaneously and highly express TNFα and IL-17A, thereby exerting highly efficient and specific killing effect while having lower toxic and side effects.

A first aspect of the present invention relates to a heterodimeric bispecific antibody comprising a first Fc chain and a second Fc chain, and a first antigen-binding functional region capable of specifically binding to TNFα and a second antigen-binding functional region capable of specifically binding to IL-17A;

wherein both the first Fc chain and the second Fc chain are Fc fragments of an immunoglobulin G comprising amino acid substitutions and together form a heterodimer that can bind to a Fc receptor;

wherein the first Fc chain and the second Fc chain are linked to the first and second antigen-binding functional regions, respectively, via a covalent bond or a linker; and wherein any one of the first Fc chain and the second Fc chain comprises amino acid substitutions at positions 366 and 399 and the other chain comprises amino acid substitutions at positions 351, 407 and 409, wherein the positions of the amino acids are numbered according to the Kabat EU index numbering system.

The first Fc chain and the second Fc chain are defined herein only for the purpose of distinguishing the two existing Fc chains, but is not intended to mean that the two has different levels of significance or shows different orders. Also, the first and the second Fc chains may be linked to the first and the second antigen-binding functional regions in any arbitrary ways, i.e., the first Fc chain may be linked to either the first or the second antigen-binding functional region, as may the second Fc chain.

In some embodiments, the amino acid substitutions for the first Fc chain and the second Fc chain are as follows,
a) L351G, L351Y, L351V, L351P, L351D, L351E, L351K, or L351W;
b) T366L, T366P, T366W, or T366V;
c) D399C, D399N, D399I, D399G, D399R, D399T or D399A;
d) Y407L, Y407A, Y407P, Y407F, Y407T, or Y407H; and
e) K409C, K409P, K409S, K409F, K409V, K409Q, or K409R.

In some embodiments, the amino acid substitutions comprise:
a) T366L and D399R substitutions in any one of the first Fc chain and the second Fc chain, and L351E, Y407L and K409V substitutions in the other chain;
b) T366L and D399C substitutions in any one of the first Fc chain and the second Fc chain, and L351G. Y407L and K409C substitutions in the other chain;

c) T366L and D399C substitutions in any one of the first Fc chain and the second Fc chain, and L351Y, Y407A and K409P substitutions in the other chain;
d) T366P and D399N substitutions in any one of the first Fc chain and the second Fc chain, and L351V, Y407P and K409S substitutions in the other chain;
e) T366W and D399G substitutions in any one of the first Fc chain and the second Fc chain, and L351D, Y407P and K409S substitutions in the other chain;
f) T366P and D399I substitutions in any one of the first Fc chain and the second Fc chain, and L351P, Y407F and K409F substitutions in the other chain;
g) T366V and D399T substitutions in any one of the first Fc chain and the second Fc chain, and L351K, Y407T and K409Q substitutions in the other chain; and
h) T366L and D399A substitutions in any one of the first Fc chain and the second Fc chain, and L351W, Y407H and K409R substitutions in the other chain.

In some embodiments, either the first Fc chain or the second Fc chain has amino acid substitutions of T366L and D399R, and the other chain has amino acid substitutions of L351E, Y407L, and K409V.

In some embodiments, both the first antigen-binding functional region and the second antigen-binding functional region are selected from the group consisting of a Fab fragment, a scFv fragment, a variable domain fragment Fv and a heavy chain variable region fragment VHH of a heavy chain antibody.

In some embodiments, both the first antigen-binding functional region and the second antigen-binding functional region are Fab fragments.

In some embodiments, one of the first antigen-binding functional region and the second antigen-binding functional region is a Fab fragment and the other is a scFv fragment.

In some embodiments, the Fab fragments comprise a first heavy chain variable region and a second heavy chain variable region that are different from each other, and a first light chain variable region and a second light chain variable region that are different from each other.

In some embodiments, the first Fc chain and the first antigen-binding functional region covalently linked thereto, and the second Fc chain and the second antigen-binding functional region covalently linked thereto form a homodimer in a solution in the presence of a reducing agent and in the absence of any other polypeptides other than the first Fc chain and the first antigen-binding functional region covalently linked thereto and the second Fc chain and the second antigen-binding functional region covalently linked thereto, in a weight ratio of less than 50% based on all polypeptide chains.

In some embodiments, the first antigen-binding functional region comprises the amino acid sequences of SEQ ID NOs: 2 and 6.

In some embodiments, the second antigen-binding functional region comprises the amino acid sequences of SEQ ID NOs: 10 and 12.

In some embodiments, the first antigen-binding functional region further comprises the amino acid sequences of SEQ ID NOs: 4 and 8.

In some embodiments, the second antigen-binding functional region further comprises the amino acid sequences of SEQ ID NOs: 4 and 14.

In some embodiments, the amino acid sequences of the bispecific antibody are the corresponding combinations of SEQ ID NOs: 2, 4, 6, 8, 10, 12 and 14. For example, SEQ ID NOs: 2, 4, 6 and 8 combine with each other, SEQ ID NOs: 10, 4, 12 and 14 combine with each other, and then, the combined two are recombined to form the bispecific antibody of the present invention.

A second aspect of the present invention relates to an isolated polynucleotide encoding the heterodimeric bispecific antibody according to the first aspect.

In some embodiments, the nucleotide sequences encoding amino acid sequences of the first antigen-binding functional region are selected from the group consisting of: SEQ ID NOs: 1 and 5.

In some embodiments, the nucleotide sequences encoding amino acid sequences of the second antigen-binding functional region are selected from the group consisting of: SEQ ID NOs: 9 and 11.

In some embodiments, the nucleotide sequences encoding amino acid sequences of the first antigen-binding functional region are further selected from the group consisting of: SEQ ID NOs: 3 and 7.

In some embodiments, the nucleotide sequences encoding amino acid sequences of the second antigen-binding functional region are further selected from the group consisting of: SEQ ID NO: 3 and 13.

In some embodiments, the sequences of the polynucleotides are the corresponding combinations of SEQ ID NOs: 1, 3, 5, 7, 9, 11 and 13. For example, SEQ ID Nos: 1, 3, 5 and 7 combine with each other and SEQ ID NOs: 9, 3, 11 and 13 combine with each other.

A third aspect of the present invention relates to a recombinant expression vector comprising the isolated polynucleotide according to the second aspect.

In some embodiments, the expression vector is the plasmid vector X0GC modified based on pCDNA.

A fourth aspect of the present invention relates to a host cell comprising the isolated polynucleotide of the second aspect, or the recombinant expression vector of the third aspect.

In some embodiments, the host cell is selected from the group consisting of a human embryonic kidney cell HEK293 cell, or a HEK293T cell, a HEK293E cell and a HEK293F cell derived from a HEK293 cell; a hamster ovary cell CHO cell, or a CHO-S cell, a CHO-dhfr-cell, a CHO/DG 44 cell and a ExpiCHO cell derived from a CHO cell; *Escherichia coli*, or *Escherichia coli* BL21, BL21 (DE3), Rosetta, Origami derived from *Escherichia coli*; a yeast, or *Pichia pastoris, Saccharomyces cerevisiae, Kluveromvces lactis*, and *Hansenula polymorpha* derived from a yeast; an insect cell, or a High 5 cell and a SF 9 cell derived from an insect cell; a plant cell; a mammalian mammary gland cell, a mammalian somatic cell.

A fifth aspect of the present invention relates to a composition comprising the heterodimeric bispecific antibody according to the first aspect or the isolated polynucleotide according to the second aspect or the recombinant expression vector according to the third aspect or the host cell according to the fourth aspect, and a pharmaceutically acceptable carrier.

A sixth aspect of the present invention relates to a method of producing the heterodimeric bispecific antibody according to the first aspect, comprising the steps of:
1) expressing the isolated polynucleotide according to the second aspect or the recombinant expression vector according to the third aspect, respectively, in a host cell;
2) reducing each protein respectively expressed in the host cells, and
3) mixing the reduced proteins and then oxidizing the mixture.

In some embodiments, the host cell is selected from the group consisting of a human embryonic kidney cell HEK293 cell, or a HEK293T cell, a HEK293E cell and a HEK293F cell derived from a HEK293 cell; a hamster ovary cell CHO cell, or a CHO-S cell, a CHO-dhfr-cell, a CHO/DG 44 cell and a ExpiCHO cell derived from a CHO cell; *Escherichia coli*, or *Escherichia coli* BL21, BL21 (DE3), Rosetta, Origami derived from *Escherichia coli*; a yeast, or *Pichia pastoris, Saccharomyces cerevisiae, Kluyveromyces lactis*, and *Hansenula polymorpha* derived from a yeast; an insect cell, or a High 5 cell and a SF 9 cell derived from an insect cell; a plant cell; a mammalian mammary gland cell, a mammalian somatic cell.

In some embodiments, the reduction step comprises 1) conducting the reduction reaction in the presence of a reducing agent selected from the group consisting of 2-mercaptoethylamine, dithiothreitol, tris(2-carboxyethyl)phosphine, or chemical derivatives thereof; 2) removing the reducing agent. For example, the reduction reaction is carried out in the presence of dithiothreitol at a concentration of 0.1 mM or higher at 4° C. for at least 3 hours. The definitions for the reducing agent and the reduction reaction conditions are applicable to other cases where a reducing agent and a reduction reaction are involved herein.

In some embodiments, the oxidization step is an air oxidation, or an oxidation reaction in the presence of an oxidizing agent selected from the group consisting of L-dehydroascorbic acid or chemical derivatives thereof. For example, the oxidization reaction is carried out in the presence of L-dehydroascorbic acid at a concentration of 0.5 mM or higher, at 4° C. for at least 5 hours.

In some embodiments, the method further comprises a step of isolation and purification.

A seventh aspect of the present invention relates to use of the heterodimeric bispecific antibody according to the first aspect and/or the isolated polynucleotide according to the second aspect and/or the recombinant expression vector according to the third aspect and/or the host cell according to the fourth aspect and/or the composition according to the fifth aspect, in the manufacture of a medicament for preventing and/or treating a disease of a subject.

An eighth aspect of the present invention relates to the heterodimeric bispecific antibody according to the first aspect and/or the isolated polynucleotide according to the second aspect and/or the recombinant expression vector according to the third aspect and/or the host cell according to the fourth aspect and/or the composition according to the fifth aspect, for use as a medicament for the prevention and/or treatment of a disease of a subject.

A ninth aspect of the invention relates to a method of preventing and/or treating a disease, comprising a step of administering to a subject in need thereof the heterodimeric bispecific antibody according to the first aspect and/or the isolated polynucleotide according to the second aspect and/or the recombinant expression vector according to the third aspect and/or the host cell according to the fourth aspect and/or the composition according to the fifth aspect.

In some embodiments, the subject is a mammal, preferably a human subject.

In some embodiments, the disease is selected from the group consisting of rheumatoid arthritis, osteoarthritis, psoriatic arthritis, ankylosing spondylitis, gouty arthritis, juvenile rheumatoid arthritis, suppurative arthritis, psoriasis, type I diabetes, multiple sclerosis, autoimmune encephalomyelitis, Crohn's disease, systemic vasculitis, dermatomyositis, mixed connective tissue disease, lupus erythematosus, idiopathic thrombocytopenic purpura, primary Sjogren's syndrome, glomerulonephritis, gout, organ-transplant rejection, asthma or atherosclerosis.

In the present invention, a novel anti-TNFα/anti-IL-17A natural antibody structure-like heterodimeric bispecific antibody has been designed, which is a highly stable heterodimeric anti-TNFα/anti-IL-17A bispecific antibody having the characteristics of a natural IgG and having no mismatched heavy and light chains. The bispecific antibody prepared by the invention can simultaneously block a TNFα signal pathway and an IL-17A signal pathway, and can exert better effects than a single therapeutic agent when being applied to treatments of complex diseases. Meanwhile, as compared with the combination treatment of a plurality of medicaments, the bispecific antibody serving as a single treatment molecule not only facilitates the application by the patients and medical workers, but also simplifies the complicated development process of new medicaments. In addition, the present invention has found that as compared with the case where IL-17A is absent, TNFα neutralizing activity of the anti-TNFα portion of the bispecific antibody is significantly enhanced when IL-17A is present, suggesting that the bispecific antibody has a stronger activity of neutralizing TNFα at the focal site having high level of IL-17A, and shows a weaker activity of neutralizing TNFα in the circulatory system having low level of IL-17A, thereby indicating that the bispecific antibody can effectively treat diseases while maintain lower toxic and side effects.

DETAILED DESCRIPTION OF THE INVENTION

Definitions

Figure 1:
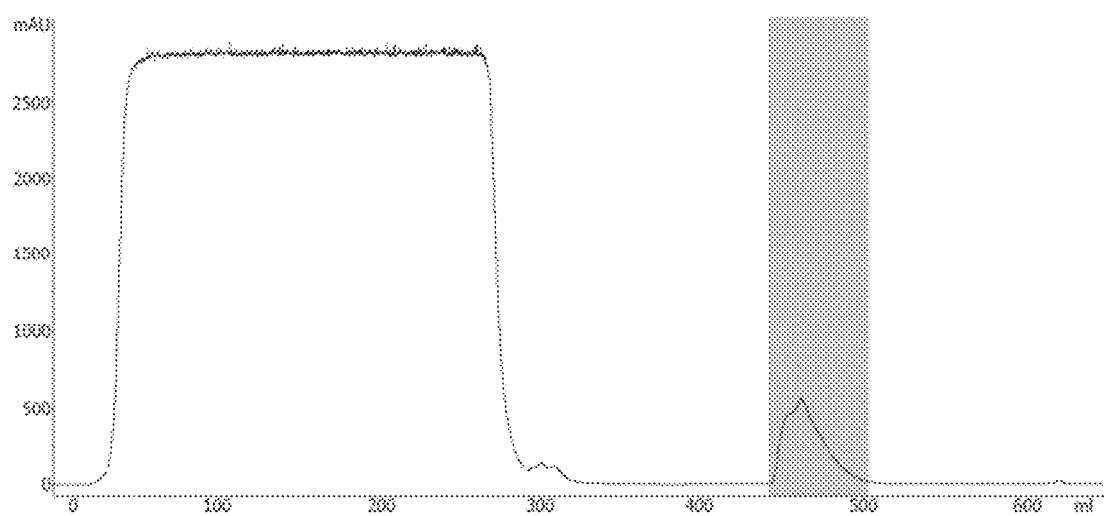
FIG. 1 shows a chromatogram of elution peaks of an anti-TNFα expression product and an anti-IL-17A expression product, wherein A is a chromatogram of an elution peak of the anti-TNFα expression product, and B is a chromatogram of an elution peak of the anti-IL-17A expression product.
Figure 1:
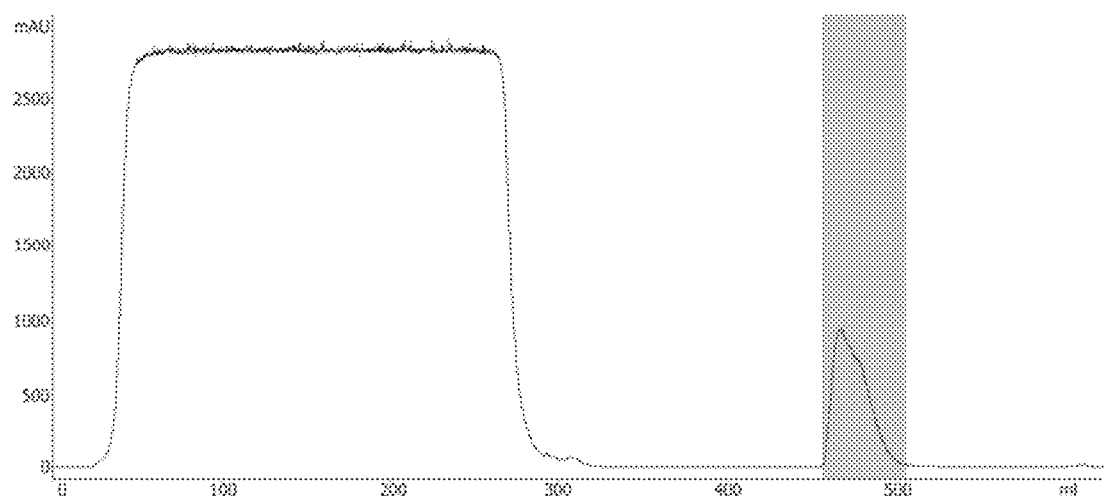

Covalent linkage means that two Fc chains, or any one of the Fc chains and an antigen-binding functional region linked thereto in a heterodimeric bispecific antibody are linked with each other via a covalent bond to form a single molecule. Among them, the Fc chains comprise a first antigen-binding functional region and a second antigen-binding functional region linked via one or more covalent bonds (e.g., a disulfide bond); the first and second Fc chains are linked to an antigen-binding functional region via a covalent linkage (e.g., an imine or amide linkage), respectively:

An antigen-binding functional region is a region which can specifically interact with a target molecule, such as an antigen, and whose action is highly selective, and a sequence that recognizes one target molecule is generally unable to recognize other molecular sequences. A representative antigen-binding functional region includes an antibody variable region, a structural variant of an antibody variable region, a receptor binding domain, a ligand binding domain, or an enzyme binding domain.

One or more disulfide bond inter-chains linkage refer to the formation of a heterodimeric fragment by linkages between the first Fc chain and the second Fc chain via one or more disulfide bonds. In the present invention, one or more disulfide bonds may be formed when the first Fc chain and the second Fc chain or the first Fc chain and the second Fc chain and the antigen-binding functional regions linked thereto are synthesized in a same cell, or may be formed by in vitro reduction-oxidation after the first Fc chain and the second Fc chain or the first Fc chain and the second Fc chain and the antigen-binding functional regions linked thereto are synthesized in different cells, respectively.

The first Fc chain and the second Fc chain refer to a binding fragment composed by a covalent linkage, wherein the covalent linkage comprises a disulfide bond, each chain comprises at least one portion of the heavy chain constant region of an immunoglobulin; and the first Fc chain and the second Fc chain are different from each other in their amino acid sequences, and comprise at least one different amino acid. As to the first and second Fc chains of the present invention, a strong, mutual, repulsive force exists between identical chains, and attractive force exists between different chains. Accordingly, the first and second Fc chains, or the first and second Fc chains and the antigen-binding functional regions linked thereto have a tendency to undergo heterodimeric formation, when co-expressed in a cell. When the first and second Fc chains, or the first and second Fc chains and the antigen binding domain linked thereto are expressed in two host cells, respectively, the first Fc chains, or the first Fc chain and the antigen binding domain linked thereto have no tendency to undergo homodimeric formation, and the second Fc chains, or the second Fc chain and the antigen binding domain linked thereto have no tendency to undergo homodimeric formation. In the present invention, when the first and second Fc chains, or the first and second Fc chains and the antigen-binding functional regions linked thereto are expressed in two host cells, respectively, and a reducing agent is present, a percentage of homodimers is less than 50%, that is, a percentage of monomers (one Fc chain or one Fc chain and one antigen-binding functional region linked thereto) is above 50%.

An immunoglobulin has a symmetrical structure having four polypeptide chains, wherein two chains are identical heavy chains which are relatively long and have a relatively high molecular weight, each including 450-550 amino acid residues and having a relative molecular weight of 55000-70000 Da; and the other two chains are identical light chains (L chains) which are relatively short and have a relatively low molecular weight, including about 210 amino acid residues and having a relative molecular weight of about 24000 Da. Sequences about 110 amino acid in length near the N-termini of the heavy and light chains of an immunoglobulin are highly variable, and are called variable regions (V regions), while the rest amino acid sequences near the C-termini thereof are relatively stable and called constant regions (C regions). The variable region in the heavy chain occupies approximately ¼ of the length of the heavy chain, and the constant region occupies approximately ¾ of the length of the heavy chain. The known five types of Igs are IgG (γ), IgA (α), IgD (δ), IgM (μ) and IgE (ε). Among them, the former three types of Igs have three constant regions in the H chain, namely, CH1, CH2 and CH3. The latter two types of Igs (IgM and IgE) have one VH region and four constant regions in the H chain, namely CH1 to CH4. The constant regions are both the framework of an immunoglobulin molecule and one of regions activating immune responses. Although examples of the invention relate to IgG, those skilled in the art would have recognized that the class of the antibodies of the invention can be switched by known methods, if desired. For example, an antibody of the invention that is initially IgM can be class-switched to an IgG antibody of the invention. In addition, class switching techniques can be used to convert one IgG subclass to another, such as from IgG1 to IgG2. Thus, the effector functions of the antibodies of the invention can be switched by isotypes to, for example, IgG1, IgG2, IgG3, IgG4, IgD, IgA, IgE or IgM antibodies for various therapeutic uses. In one embodiment, the antibody of the invention is an IgG1 antibody, such as IgG1, κ.

A part of the constant region of the present disclosure includes at least an interaction region of the first Fc chain and the second Fc chain, and in the case of IgG, this region is located at some amino acid positions of CH3 domain and includes at least GLN 347, TYR 349, THR 350, LEU 351, SER 354, ARG 355, ASP 356, GLU 357, LYS 360, SER 364, THR 366, LEU 368, LYS 370, ASN 390, LYS 392, THR 394, PRO 395, VAL 397, ASP 399, SER 400, PHE 405, TYR 407, LYS 409, and LYS 439.

The first Fc chain and the second Fc chain each linked to one antigen-binding functional region via a covalent bond or a linker indicate the first Fc chain and the second Fc chain each linked to an antigen-binding fragment of an antibody, or a single chain antibody capable of recognizing an antigen, or other antibody fragment variant capable of recognizing an antigen, or a receptor capable of recognizing a ligand, or a ligand capable of recognizing a receptor via a covalent bond or a linker. The covalent bond is a kind of chemical bonding, in which two or more atoms together use their outer electrons, to reach electronic saturation state in an ideal situation, thus forming a relatively stable chemical structure named a covalent bond, or the interaction among atoms is formed by shared electron pair. Atoms of the same element or atoms of different elements may be all linked via a covalent bond. The covalent bond between the first Fc chain and the second Fc chain of the invention includes, but is not limited to, an amide bond formed by dehydration between an amino group of an amino acid of one molecule and a carboxyl group of an amino acid of another molecule, or an amide bond or imine bond formed between an aldehyde group of ethylene glycol or polyethylene glycol or other compound or a polymer thereof and an amino group of an amino acid of one molecule; wherein the linker is one stretch of amino acid sequence or one compound or one multimer of one compound capable of linking two polypeptide chains via a covalent bond, wherein the one stretch of amino acid sequence includes, but is not limited to, a small peptide, such as GGGGSGGGGSGGGGS, and the first Fc chain or the second Fc chain, and a single-chain antibody capable of recognizing an antigen, or other antibody fragment structural variant capable of recognizing an antigen via an amide bond.

The first Fc chain and the second Fc chain have a tendency to undergo heterodimeric formation and no tendency to undergo homodimeric formation, which means that as in the first Fc chain and the second Fc chain, a repulsive force exists between identical polypeptide chains and an attractive force exists between different polypeptide chains, and therefore, the first Fc chain and the second Fc chain, or the first and second Fc chains and the antigen-binding functional regions linked thereto have a tendency to undergo heterodimeric formation, when co-expressed in a cell. When the first Fc chain and the second Fc chain, or the first and second Fc chains and the antigen-binding functional regions linked thereto are expressed in two host cells, respectively, the first Fc chains, or the first Fc chain and the antigen-binding functional region linked thereto have no tendency to undergo homodimeric formation, and the second Fc chains, or the second Fc chain and the antigen-binding functional region linked thereto also have no tendency to undergo homodimeric formation.

The Kabat EU index numbering system means that Kabat assigns a number to each amino acid in an antibody sequence using a method, and such a method of assigning residue the numbers has become a standard method in the field. The Kabat's protocol is extendible to other antibodies not present in his study by aligning a target antibody with one of the consensus sequences in Kabat with reference to conserved amino acids.

The Fc domain refers to a fragment crystallizable (Fc), corresponds to CH2 and CH3 domains of an Ig, and is a site where an Ig interacts with an effector molecule or a cell.

IgG is an abbreviation for immunoglobulin G (IgG), and is the main type of antibody in the serum. Human IgG has four subclasses, namely IgG1, IgG2, IgG3 and IgG4, based on antigenic differences in r-chains in the IgG molecules.

A half-antibody molecule refers to a structure formed by one heavy chain and one light chain of an antibody, wherein the heavy chain and the light chain may be linked via or not via a covalent bond, and is a monovalent antibody structure recognizing an antigen. A Fab fragment is a molecule-recognizing sequence, and a fragment of antigen binding (Fab), and corresponds to two arms of an antibody molecule, consisting of a complete light chain and VH and CH1 domains of a heavy chain. scFv is a molecule-recognizing sequence, and is a structural variant of an antibody fragment obtained by genetic engineering modification of a light chain variable region and a heavy chain variable region of an antibody. An extracellular region of a membrane receptor is a molecule-recognizing sequence, and the membrane receptor generally comprises an extracellular region located outside the cell that recognizes and binds to the corresponding antigen or ligand, a transmembrane region that anchors the receptor onto the cell surface, and an intracellular region in a cell that has kinase activity or transfers a signal. A ligand of the cell membrane receptor refers to a protein, a small peptide or a compound that may be recognized and bound by the extracellular region of a membrane receptor. Cytokines are low-molecular weight soluble proteins that are produced by various types of cells induced by immunogens, mitogens or other stimulants, and have various functions such as regulations of innate immunity and adaptive immunity, hematopoiesis, cell growth, APSC pluripotent cell and damage tissue repair, etc. Cytokines may be classified into interleukins, interferons, tumor necrosis factor superfamilies, colony stimulating factors, chemokines, growth factors, etc. A protein expression tag means an amino acid sequence added at the N-terminus or C-terminus of a target protein, and may be small peptides or a long amino acid sequence. Addition of a tag may be advantageous for correct folding of proteins, isolation and purification of proteins, and decreasing intracellular degradation of proteins. Tags frequently used may include, but not limited to HA, SUMO, His, GST, GFP and Flag.

There is no limitation in the antibodies applicable to the heterodimeric bispecific antibody of the present invention. Preferably, the antibodies known in the art to be useful in the treatment and/or prevention of diseases may be applied to the present invention.

The heterodimeric bispecific antibody of the invention may have one or more substitutions, deletions, additions and/or insertions. For example, certain amino acids can substitute other amino acids in the protein structure without significant loss of the binding capacity to other polypeptides (e.g., antigens) or cells. Since the binding capacity and protein properties determine the bioactivities and functions of a protein, substitutions of some amino acids in the protein sequence may cause no significant loss of its biological effectiveness or activities.

In many cases, a polypeptide variant includes one or more conservative substitutions. "Conservative substitutions" refers to those in which amino acids in the polypeptide are replaced by other amino acids having similar properties, such that one skilled in the art of peptide chemistry would anticipate that the secondary structure and hydrophilic nature of the polypeptide are substantially unchanged.

Amino acid substitutions are generally based on relative similarity of the amino acid side-chain substituents, such as hydrophobicity, hydrophilicity, charges, size, etc. Exemplary alternatives that take various aforementioned characteristics into consideration are well known to those skilled in the art and include arginine and lysine; glutamic acid and aspartic acid; serine and threonine; glutamine and asparagine; and valine, leucine and isoleucine.

As used herein, the term "identity" has the meaning commonly known in the art, and those skilled in the art also are familiar with the rules, criteria for determining identity between different sequences, and "identity" refers to the percentage of homology between residues of a polynucleotide or polypeptide sequence variant and residues of an non-variant sequence after aligning the sequences and introducing gaps (if necessary, to obtain the maximum percentage homology). In the present invention, when the definition of identity is satisfied, it is also required that the obtained variant sequence has the biological activities possessed by the parent sequence. Methods and means for screening variant sequences using the above activities are well known to those skilled in the art. Such variant sequences could be readily obtained by those skilled in the art in light of the present disclosure. In specific embodiments, the polynucleotide and polypeptide variants have at least about 70%, at least about 75%, at least about 80%, at least about 90%, at least about 95%, at least about 98%, or at least about 99%, or at least about 99.1%, 99.2%, 99.3%, 99.4%, 99.5%, 99.6%, 99.7%, 99.8%, or 99.9% polynucleotide or polypeptide identity with the polynucleotide or polypeptide described herein. Due to the redundancy of the genetic codons, variants of these sequences encoding the same amino acid sequence will exist.

Another embodiment of the present invention provides a polynucleotide composition capable of hybridizing to the polynucleotide sequences provided by the present invention or fragments thereof or complementary sequences thereof under moderately to highly stringent hybridization conditions. Hybridization techniques are well known in the art of molecular biology. For the purposes of illustration, suitable moderately stringent hybridization conditions for testing the hybridization of the polynucleotides of the present invention to another polynucleotides include pre-washing with a solution of 5×SSC, 0.5% SDS, 1.0 mM EDTA (pH 8.0); hybridizing in 5×SSC at 50-60° C. overnight; and washing twice with 2×, 0.5× and 0.2×SSC containing 0.1% SDS for 20 minutes at 65° C. Those skilled in the art understand that the stringency of hybridization may be readily manipulated, for example, by changing the salt content of the hybridization solution and/or the hybridization temperature. For example, in another embodiment, suitable highly stringent hybridization conditions include those described above, except that the hybridization temperature is increased, e.g., to 60-65° C. or 65-70° C.

The host cell of the present invention may be any cell for expressing a foreign gene, and may include, but not limit to E. coli, a yeast, an insect cell, a plant cell, a mammalian cell.

The vector of the present invention includes a vector that may replicate in any type of cells or organisms, including, for example, plasmids, phages, cosmids, and mini-chromosomes. In some embodiments, the vector comprising the polynucleotide of the present invention is a vector suitable for propagation or replication of a polynucleotide, or a vector suitable for expression of the polypeptide of the present invention. Such vectors are known in the art and are commercially available.

The "vector" includes a shuttle vector and an expression vector. Generally, a plasmid construct also includes an origin of replication (e.g., ColE 1 origin of replication) and a selectable marker (e.g., ampicillin or tetracycline resistance) which are for plasmid replication and selection in bacteria, respectively. The "expression vector" refers to a vector including control sequences or regulatory elements which are required for expression of the antibody of the present invention, including antibody fragments, in a bacterial or eukaryotic cell.

The vector of the present invention may be any vector used for foreign gene expression, including, but not limited to, a plasmid vector, wherein the plasmid vector includes at least an origin of replication, a promoter, a gene of interest, a multiple clone site, a selection marker gene, and preferably, the vector of the present invention includes, but is not limited to, a plasmid vector obtained based on pCDNA such as X0GC vector.

The subject of the present invention includes birds, reptiles, mammals, etc. Preferably, the mammal includes a rodent and a primate. Preferably, the primate includes a human.

The scope of diseases involved in the present invention includes, but is not limited to, inflammations, autoimmune diseases, preferably, the disease is selected from the group consisting of rheumatoid arthritis, osteoarthritis, psoriatic arthritis, ankylosing spondylitis, gouty arthritis, juvenile rheumatoid arthritis, suppurative arthritis, psoriasis, type I diabetes, multiple sclerosis, autoimmune encephalomyelitis, Crohn's disease, systemic vasculitis, dermatomyositis, mixed connective tissue disease, lupus erythematosus, idiopathic thrombocytopenic purpura, primary Sjogren's syndrome, glomerulonephritis, gout, organ-transplant rejection, asthma or atherosclerosis, more preferably, the disease is selected from the group consisting of rheumatoid arthritis, osteoarthritis, psoriatic arthritis, gouty arthritis, juvenile rheumatoid arthritis, suppurative arthritis.

The pharmaceutically acceptable carrier means a pharmaceutical carrier commonly used in the pharmaceutical art, for example, diluents, excipients, water, etc., fillers such as starch, sucrose, lactose, microcrystalline cellulose, etc.: binders such as cellulose derivatives, alginates, gelatin, and polyvinylpyrrolidone; wetting agents such as glycerin; disintegrating agents such as sodium carboxymethyl starch, hydroxypropyl cellulose, croscarmellose, agar, calcium carbonate and sodium hydrogencarbonate, etc.; absorption enhancers such as quaternary ammonium compounds; surfactants such as cetanol, sodium lauryl sulfate, etc.; adsorption carriers such as kaolinite and bentonite; lubricants such as talc, calcium and magnesium stearate, aerosil, polyethylene glycol, etc. Other adjuvants such as flavoring agents, sweeteners, etc. may also be added to the composition.

The invention will now be further illustrated with reference to the following non-limiting examples. It will be understood by those skilled in the art that various modifications may be made therein without departing from the spirit and scope of the present invention, and such modifications are also included in the scope of the present invention.

The following experimental methods are all common methods unless otherwise specified, and the experimental materials used are readily available from commercial companies unless otherwise specified. The various antibodies used in the following Examples of the present invention are all standard antibodies commercially available.

Examples

Example 1. Construction of the Vector of Anti-TNFα/Anti-IL-17A Heterodimeric Antibody Molecule X0GC expression vectors including heavy and light chains of anti-human TNFα antibody (Adalimumab) were constructed, respectively. The sequences of the variable regions of the antibody are originated from drugbank database. The nucleotide sequence of the variable region of the light chain is set forth in SEQ ID NO: 1, and the amino acid sequence thereof is shown in SEQ ID NO: 2; the nucleotide sequence of the constant region of the light chain is set forth in SEQ ID NO: 3, and the amino acid sequence thereof is shown in SEQ ID NO: 4; the nucleotide sequence of the variable region of the heavy chain is set forth in SEQ ID NO: 5, and the amino acid sequence thereof is shown in SEQ ID NO: 6; the nucleotide sequence of the constant region of the heavy chain is shown in SEQ ID NO: 7, and the amino acid sequence thereof is set forth in SEQ ID NO: 8. The variable region and the constant region of the light chain, and the variable region and the constant region of the heavy chain were amplified by PCR. In all PCR reactions of the present disclosure, Phusion super-fidelity DNA polymerase (F-530L) of NEB Inc. was used. PCR primers were designed conventionally according to the principle of base complementation and the need for restriction enzyme cutting sites. Each reaction system consists of 8.9 µl of H$_2$O, 4 µl of 5×Phusion super-fidelity DNA polymerase buffer, 4 µl of 1 mM dNTPs, 1 µl of forward primer, 1 µl of reverse primer, 0.1 µl of Phusion super-fidelity DNA polymerase, 1 µl of the template. PCR products of the variable and constant regions were electrophoresed on 1.5% agarose gel, and corresponding fragments were recovered using a DNA recovery kit (Promega, A9282, the same applies hereinafter). The recovered variable region fragment and constant region fragment used as templates, and the forward primer of the variable region and the reverse primer of the constant region were used to perform next round of PCR. Then, corresponding fragments were recovered to obtain full-length fragments of the heavy chain and the light chain. The X0GC vector and the full-length fragments were enzymatically digested with EcoRI (NEB, cat #R3101L) and HindIII (NEB, cat #R3104L). The enzyme digestion conditions consist of 2 µl of 10×buffer 3, 0.5 µl of each of EcoRI and HindIII, 3 µl of the full-length fragments recovered from the gel, and 14.5 µl of H$_2$O. The digestion system was allowed to react at 37° C. for 3 hours. The digested products were ligated using T4 DNA ligase (NEB, cat #M0202V) (the same applies hereinafter), and the reaction conditions consist of 2 µl of 10×ligase buffer, 0.5 µl of ligase, 3 µl of the full-length fragments recovered from the gel, 3 µl of the X0GC vector recovered from the gel, 11.5 µl of H$_2$O, which were ligated at room temperature for 12 hours. The ligation product was transformed into *E. coli* competent cells DH5a (Tiangen, CB 104, the same applies hereinafter). The X0GC expression vectors comprising the heavy and light chains of the antibody were obtained for expression of the heavy and light chains of the antibody in eukaryotic cells, respectively.

X0GC expression vectors comprising the heavy and light chains of the anti-human IL-17A antibody (BJHM) were constructed, respectively. The sequences of the antibody variable regions are originated from the patent application WO 2018050028. The nucleotide sequence of the variable region of the light chain is set forth in SEQ ID NO: 9, and the amino acid sequence thereof is shown in SEQ ID NO: 10; the nucleotide sequence of the constant region of the light chain is set forth in SEQ ID NO: 3, and the amino acid sequence thereof is shown in SEQ ID NO: 4; the nucleotide sequence of the variable region of the heavy chain is set forth in SEQ ID NO: 11, and the amino acid sequence thereof is shown in SEQ ID NO: 12; the nucleotide sequence of the constant region of the heavy chain is set forth in SEQ ID NO:13, and the amino acid sequence thereof is shown in SEQ ID NO: 14. The X0GC expression vectors comprising the heavy and light chains of the antibody were obtained for expression of the heavy and light chains of the antibody in eukaryotic cells, respectively.

Example 2. Expression of the Anti-TNFα/Anti-IL-17A Heterodimeric Antibody Molecule The expression vectors comprising the heavy and light chains of the anti-human or anti-mouse TNFα antibody were transfected into ExpiCHO cells (ExpiHO™ Cells, cat #A29127, invitrogen), respectively, and the expression vectors comprising the heavy and light chains of the anti-human or anti-mouse IL-17A antibody were also transfected into ExpiCHO cells, respectively. One day before transfection, cells were seeded at a density of 3.5×10$^6$ cells/mL. On the day of transfection, cells were diluted with fresh ExpiCHO expression medium (ExpiHO™ Expression Medium, cat #A29100-01, invitrogen) to a final density of 6×10$^6$ cells/mL. Plasmids were taken out according to transfection volume to a final concentration of 0.5 ug/ml, and plasmids were diluted to 4% of the transfection volume using OptiPRO™ SFM medium (OptiPRO™ SFM, cat #12309-019, invitrogen), and mixed homogeneously by inversion. The ExpiFectamine™ transfection reagent (ExpiFectamine™ CHO Transfection Kit, cat #A29129, invitrogen) in an amount of 6.4 times the plasmid volume was taken out, and diluted to 4% of the Transfection volume using OptiPRO™ SFM medium, and mixed homogeneously by inversion. To the diluted plasmids was added the diluted transfection reagent, and the mixture was gently mixed, and allowed to stand at room temperature for 1-5 minutes, and slowly added dropwise into the cells. Then, the cells were placed in a cell incubator (CO$_2$ concentration: 8%) at 37° C. for 20 hours on a shaker at 120 rpm. To the cells, 0.006 times the transfection volume of ExpiCHO™ Enhancer (ExpiFectamine™ CHO Transfection Kit, cat #A29129, invitrogen) and 0.24 times the transfection volume of ExpiCHO™ Feed (ExpiCHO™ Feed, cat #A29101-02, invitrogen) were slowly added dropwise. Incubation was performed on a shaker at 120 rpm at 32° C. Cell culture supernatants transfected for 10 days were collected by centrifugation.

Expression levels were determined by ELISA assay. Before purification using a chromatographic column, the precipitate was removed by filtering through a 0.2 µm filter membrane. This procedure was performed at 4° C.

Example 3. Purification of the Expression Product of the Anti-TNFα/Anti-IL-17A Heterodimeric Antibody Molecule Purification was performed at room temperature using AKTA explorer type 100 protein purification system (GE Healthcare) and the affinity chromatography column, Mabselect SuRe (16 mm I.D., 27 ml, GE Healthcare). The column was first equilibrated with mobile phase A (20 mM sodium phosphate buffer, pH 7.4). After baseline stabilization, the supernatants of the cells as treated above were loaded at a flow rate of 5 ml/min. After loading, equilibration was performed using mobile phase A. The samples were the anti-TNFα expression products and the anti-IL-17A expression products expressed in Example 2, respectively. Thereafter, mobile phase B1 (mobile phase A containing 1M sodium chloride) was firstly used to elute 3 column volumes, and then equilibration solution A (20 mM sodium phosphate buffer, pH 7.4) was used to wash one column volume; finally, mobile phase B2 (100 mM glycine, 10 mM sodium chloride, pH 3.3) was used to elute 5 column volumes to collect an elution peak, i.e. the peak of the protein of interest; the flow rate during the above elution steps was all 5 ml/min. The chromatogram of the elution peak of the anti-TNFα antibody is shown in FIG. 1A, and the chromatogram of the elution peak of the anti-IL-17A antibody is shown in FIG. 1B. The indicated elution peaks (grey area as shown) were collected and pH was adjusted to 7.0 by dropwise addition of 1M Tris solution.

Figure 2:
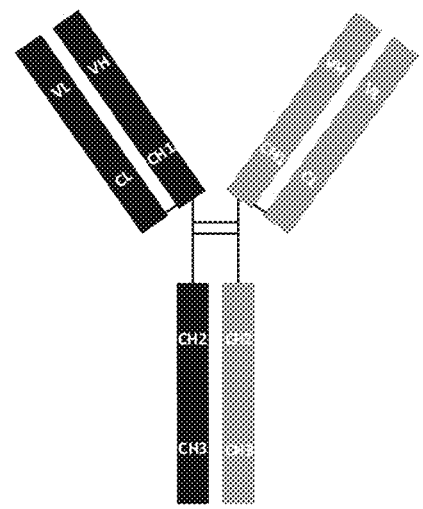
FIG. 2 shows a structure of an anti-TNFα/anti-IL-17A heterodimeric antibody molecule.

Example 4. Purification of the Anti-TNFα/Anti-IL-17A Heterodimeric Antibody Molecule The structure of the anti-TNFα/anti-IL-17A heterodimeric antibody molecule is illustrated in FIG. 2.

Figure 3:
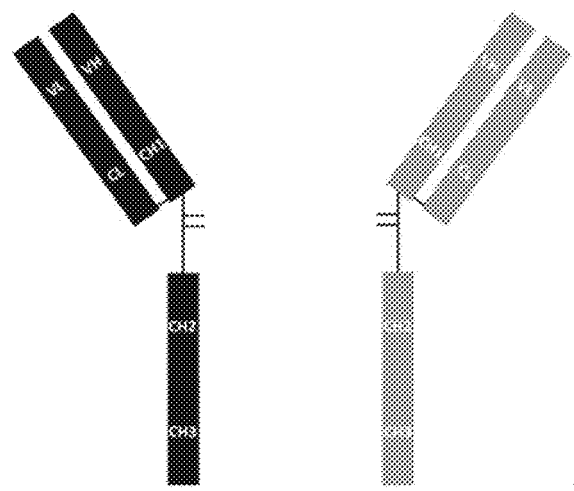
FIG. 3 shows a structure of a half-antibody molecule comprising one heavy chain and one light chain.
Figure 4:
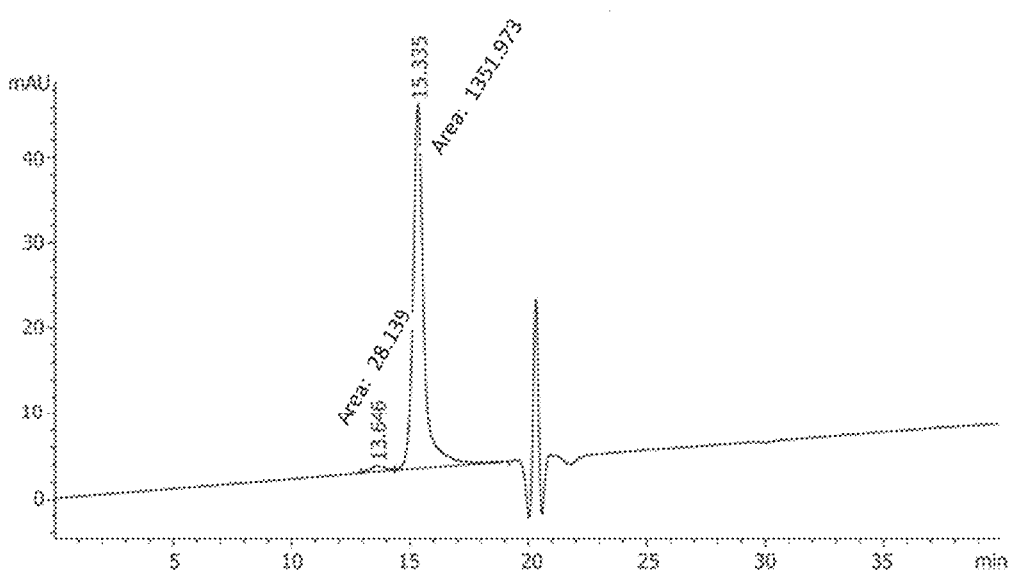
FIG. 4 shows results of SEC analysis of a half-antibody molecule comprising one heavy chain and one light chain, where A is an anti-TNFα half-antibody molecule with a purity of 98%, and B is an anti-IL-17A half-antibody molecule with a purity of 90.2%.
Figure 4:
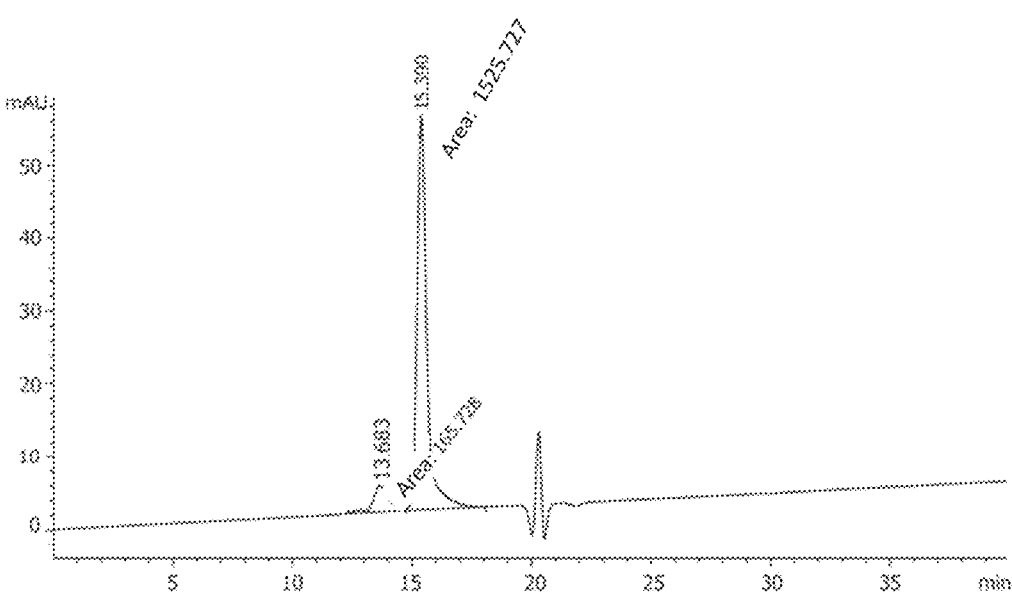

The anti-TNFα and the anti-IL-17A expression products obtained in Example 3 above by purification on a Mabselect SuRe (16 mm I.D., 27 ml, GE Healthcare) column were subjected to in vitro restitution to obtain a heterodimer. First, the protein solutions purified and collected above were concentrated by ultrafiltration through an ultrafiltration concentrating tube (nominal molecular weight cut-off 10 kDa), and the solution was replaced with phosphate buffer saline (PBS) (pH=7.4). The obtained anti-TNFα and anti-IL-17A expression products were adjusted to 1 mg/ml with addition of PBS, and 1/200 times the final volume of 1M DTT was added such that the final concentration of DTT was 5 mM, respectively. The reduction was carried out at 4° C. (3-8 hours), and the disulfide bonds were opened through the reduction process, and the disulfide bonds of the hinge regions of a small amount of homodimeric antibody molecules contained in the anti-TNFα and anti-IL-17A expression products were also opened, thereby forming a half-antibody molecule comprising one heavy chain and one light chain, of which the structure is as illustrated in FIG. 3. The reduced samples were analyzed by SEC-HPLC containing 1 mM DTT reducing agent in the mobile phase buffer. The results are as shown in FIG. 4A and FIG. 4B. The weight ratios of the anti-TNFα and anti-IL-17A homodimeric molecules were all less than 10%. Consistent therewith, the weight ratios of the half-antibody molecules were all more than 90%.

Figure 5:
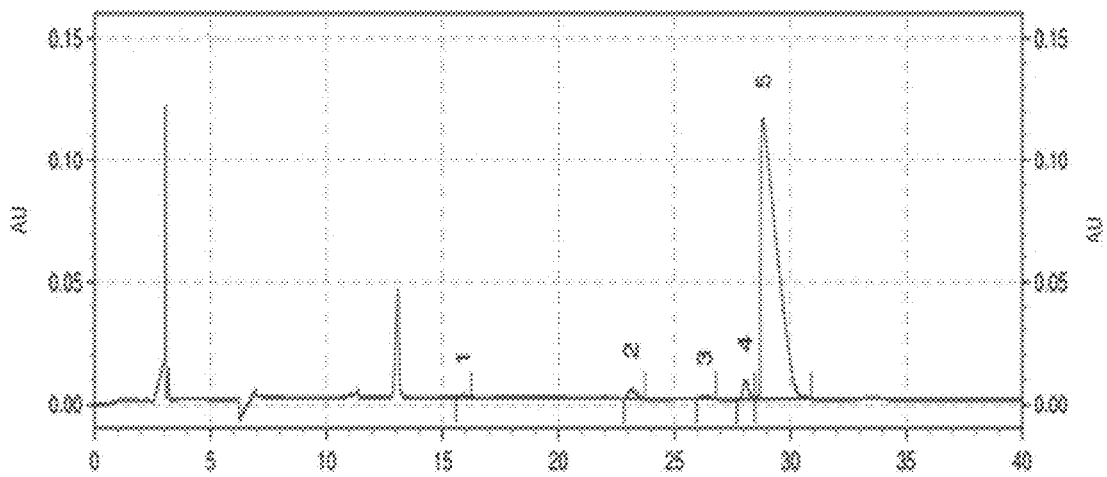
FIG. 5 shows results of non-reducing capillary electrophoresis of an anti-TNFα/IL-17A heterodimeric antibody molecule, wherein peak 1 corresponds to a single light chain, peak 2 corresponds to one heavy chain plus one light chain, peak 3 corresponds to two heavy chains, peak 4 corresponds to two heavy chains plus one light chain, peak 5 corresponds to two heavy chains plus two light chains.

Thereafter, the reduced anti-TNFα and anti-IL-17A half-antibody molecules were mixed in an equimolar ratio, and a restitution reaction was carried out for 24 hours at 4° C. During restitution, the anti-TNFα and anti-IL-17A half-antibody molecules formed the heterodimeric bispecific antibody comprising both the anti-TNFα and anti-IL-17A half-antibody molecules via non-covalent interaction between CH2/CH3. Then, the protein solution was concentrated by ultrafiltration through an ultrafiltration concentrating tube (nominal molecular weight cut-off of 10 kDa), and the solution was replaced with a phosphate solution (PBS, pH=7.4) to terminate the reduction. The solution was subjected to oxidation in the air or with an oxidizing agent to allow the formation of disulfide bonds of the heterodimeric bispecific antibody. The oxidation reactions were as follows: 100 mM L-dehydroascorbic acid as the oxidizing agent was added, and the final protein concentration of the protein became 1 mg/ml and the final concentration of the oxidizing agent became 1 mM, and oxidation was performed at 4° C. for 24 hours. The sample obtained by the above oxidation reaction was subjected to capillary electrophoresis analysis, and the results are as shown in FIG. 5.

Figure 6:
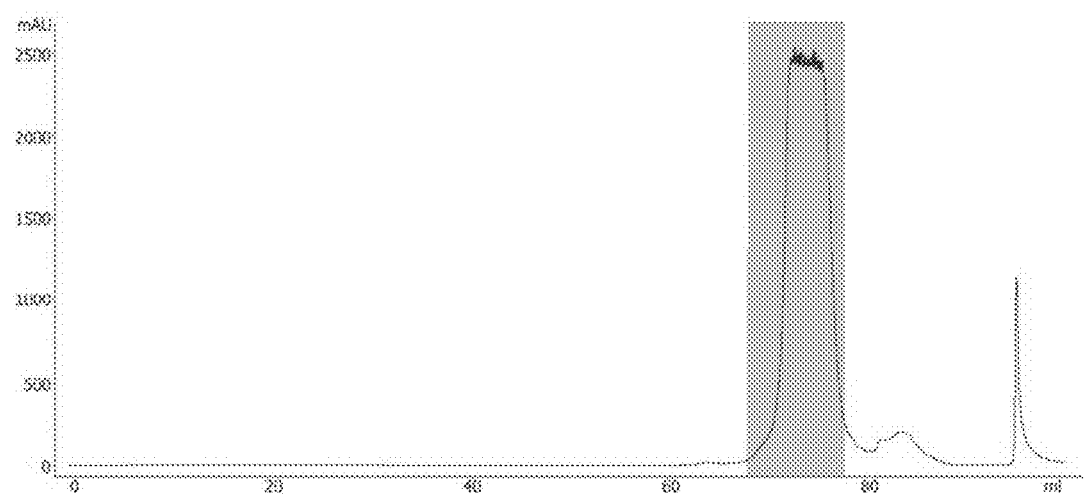
FIG. 6 shows an elution peak of an anti-TNFα/anti-IL-17A heterodimeric antibody molecule.
Figure 7:
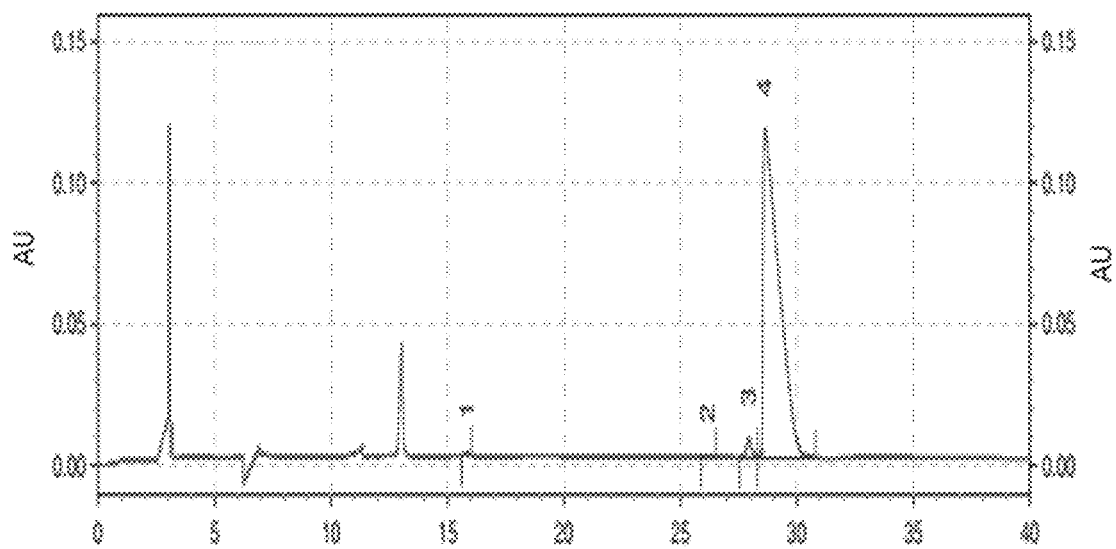
FIG. 7 shows results of non-reducing capillary electrophoresis of a finally purified anti-TNFα/anti-IL-17A heterodimeric antibody molecule, where peak 1 corresponds to a single light chain, peak 2 corresponds to two heavy chains, peak 3 corresponds to two heavy chains plus one light chain, and peak 4 corresponds to two heavy chains plus two light chains.
Figure 8:
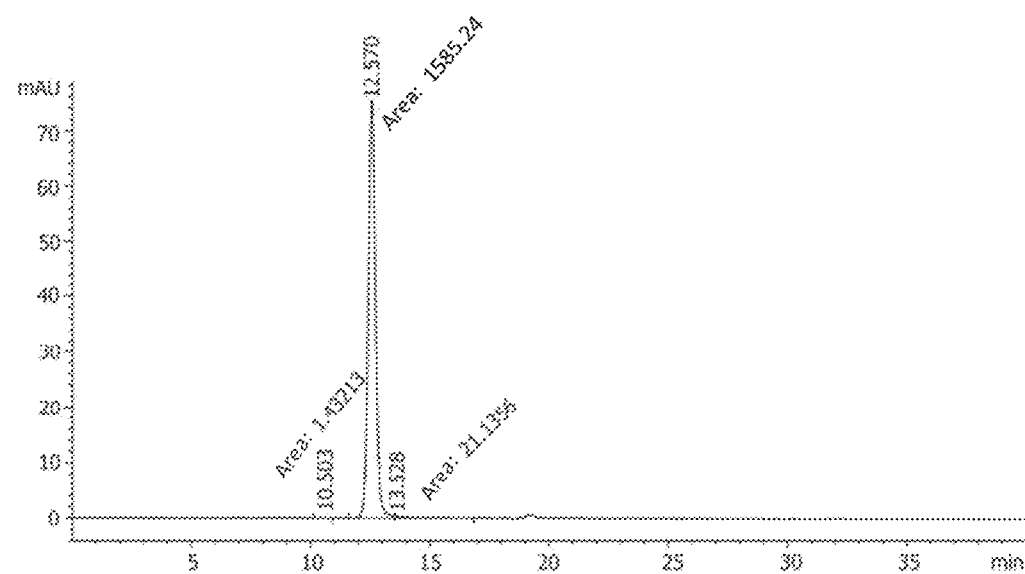
FIG. 8 shows results of SEC analysis of an anti-TNFα/anti-IL-17A heterodimeric antibody molecule with a purity of 99.9%.

The heterodimeric molecules obtained by the above reduction/oxidation processes of the anti-TNFα and anti-IL-17A half-antibody molecules were concentrated by ultrafiltration through an ultrafiltration concentrating tube (nominal molecular weight cut-off of 10 kDa), and the solution was replaced with 10 mM sodium phosphate buffer (pH 5.8). Purification was performed at 4° C. using an AKTA explorer type 100 protein purification system (GE Healthcare) and an ion chromatography column Source 15S (10 mm I.D., 2 ml, GE Healthcare). First, mobile phase A (10 mM sodium phosphate, pH 7.0) was used to equilibrate the chromatography column. After baseline stabilization, the above-treated protein solution was loaded at a flow rate of 1 ml/min. After loading the sample, equilibration was performed using mobile phase A. Thereafter, 20 column volumes (0% B-100% B, 80 min, flow rate: 0.5 ml/min) were washed with a gradient from A (10 mM sodium phosphate, pH 5.8) to B (10 mM sodium phosphate, pH 5.8). The main elution peak was collected (FIG. 6), and the collected protein solution was concentrated by ultrafiltration through an ultrafiltration concentrating tube (nominal molecular weight cut-off 10 kDa). The solution was replaced with a phosphate solution (PBS, pH=7.4), sterilized by filtration and then stored at 4° C. The anti-human TNFα/anti-human IL-17A heterodimeric antibody was named BH1657. The purified products were analyzed by capillary electrophoresis, and the results are as shown in FIG. 7. As a result of purity analysis by SEC-HPLC, the purity was 99.9%, as shown in FIG. 8.

Example 5. Preparation of the Anti-Mouse TNFα/Anti-Mouse IL-17A Heterodimeric Antibody Molecule According to the methods described in Examples 1-4, X0GC expression vectors comprising the heavy and light chains of the anti-mouse TNFα antibody (sequences of the variable regions of the heavy and light chains were cloned from V1q hybridoma cells secreting rat anti-mouse TNFα antibody (Echtenacher et al., J. Immunol. 145: 3762-3766 (1990)) and X0GC expression vectors comprising the heavy and light chains of the anti-mouse IL-17A antibody (sequences the variable regions of the heavy and light chains were originated from U.S. Pat. No. 7,846,443, 1D10) were simultaneously constructed in the present invention, respectively. For the anti-mouse TNFα antibody, the nucleotide sequence of the constant region of the light chain is set forth in SEQ ID NO: 3, and the amino acid sequence thereof is shown in SEQ ID NO: 4; the nucleotide sequence of the constant region of the heavy chain is set forth in SEQ ID NO: 7, and the amino acid sequence thereof is shown in SEQ ID NO: 8. For the anti-mouse IL-17A antibody, the nucleotide sequence of the variable region of the light chain is set forth in SEQ ID NO: 15, and the amino acid sequence thereof is shown in SEQ ID NO: 16; the nucleotide sequence of the constant region of the light chain is set forth in SEQ ID NO: 3, and the amino acid sequence thereof is shown in SEQ ID NO: 4; and the nucleotide sequence of the variable region of the heavy chain is set forth in SEQ ID NO: 17, and the amino acid sequence thereof is shown in SEQ ID NO: 18; the nucleotide sequence of the constant region of the heavy chain is set forth in SEQ ID NO: 13, and the amino acid sequence thereof is shown in SEQ ID NO: 14. The X0GC expression vectors comprising the heavy and light chains of these antibodies were then obtained, and used for expressions of the heavy and light chains of the antibodies in eukaryotic cells, respectively. The anti-mouse TNFα/anti-mouse IL-17A heterodimeric antibody, designated BH1654, was then obtained by expression/purification, having purity similar to that of BH1657 (data not shown).

Example 6. Stability of the Anti-TNFα/Anti-IL-17A Heterodimeric Antibody Molecule A well-sealed 1 mg/mL anti-TNFα/anti-IL-17A heterodimeric antibody (BH1657) sample obtained by Example 4 was placed in a 40° C. calorstat (Boxun Biochemical incubator BSP-400). 10 μg of sample was taken at the corresponding time points (baseline (week 0), week 1, week 4, week 6, week 8) for size exclusion high performance liquid chromatography (SEC-HPLC). The above SEC-HPLC conditions were as follows: (1) size exclusion column: waters xbridge BHE2003.5 um, 7.8 mm×30 cm; (2) mobile phase: 0.1M PB pH 6.7+0.1M $Na_2SO_4$, pH 6.7. (3) flow rate: 0.6 mL/min; (4) ultraviolet detection wavelength: 280 nm; (5) acquisition time: 40 min. The instrument used was Agilent 1200 Infinity chromatograph, the chromatogram was recorded using an Agilent ChemStation and the ratio of the remaining monomers was calculated. As shown in Table 1, the main peak ratio has small change under the experimental condition of 40° C., so the anti-TNFα/anti-IL-17A heterodimeric antibody is considered to have better thermal stability.

TABLE 1

Stability of the anti-TNFα/anti-IL-17 heterodimer

|  | Main peak ratio (%) | High molecular weight impurity ratio (%) | Low molecular weight impurity ratio (%) | Main peak decrease ratio (%)/day |
|---|---|---|---|---|
| week 0 | 97.08 | 0 | 2.92 | / |
| week 1 | 96.49 | 0 | 3.51 | 0.08 |
| week 4 | 92.17 | 0.12 | 7.71 | 0.17 |
| week 6 | 92.15 | 0.25 | 7.60 | 0.12 |
| week 8 | 89.41 | 0.64 | 9.95 | 0.14 |

Example 7. Target Binding Activity of the Anti-TNFα/Anti-IL-17A Heterodimeric Antibody The kinetic association constants of the anti-TNFα/anti-IL-17A heterodimeric antibody (BH1657) to its antigens TNFα and IL-17A were determined using a Biacore X100 instrument. The instrument uses the optical surface plasma resonance technology to detect the association and dissociation between the molecules coupled and coated on the biochip and the molecules to be detected. The main reagent used was a Protein A chip (GE Healthcare, 29-1275-57). The experimental procedure is briefly described as follows: BH1657 samples and control samples (the anti-TNFα monoclonal antibody and the anti-IL-17A monoclonal antibody), human TNFα and human IL-17A were diluted in 1×HBS-EP+solution (10 mM HEPES, 150 mM NaCl, 3 mM EDTA, 0.05% surfactant P20, pH 7.4), respectively. During the capture-binding phase, 1 μg/mL BH1657 sample or control sample was injected at a rate of 10 μL/min for 60 seconds; during the binding phase, human TNFα at different concentrations and solvent control (1×HBS-EP+solution) were injected at a rate of 30 μL/min for 120 seconds, respectively, or human IL-17A at different concentrations and solvent control were injected at 30 μL/min for 60 seconds, respectively; during the dissociation phase, 1×HBS-EP+solution was injected at a rate of 10 μL/min for 1800 seconds. Regeneration condition was 10 mM glycine salt solution, pH 1.5. Association kinetic constants and dissociation kinetic constants were analytically calculated by Biacore X100 control software.

The association kinetics constants, dissociation kinetics constants and equilibrium dissociation constants of BH1657, human TNFα and human IL-17A are shown in Tables 2 and 3, respectively. The results show that the anti-TNFα/anti-IL-17A heterodimer retains antigen binding activity consistent with that of the parental monoclonal antibody.

TABLE 2

Kinetic constants for BH1657 binding to human TNFα

| Sample | $k_{on}$ (1/Ms) | $k_{off}$ (1/s) | $K_D$ (m) |
|---|---|---|---|
| The anti-TNFα monoclonal antibody | 1.96E+06 | 3.82E−05 | 1.95E−11 |
| BH1657 | 2.45E+06 | 4.98E−05 | 2.03E−11 |

TABLE 3

Kinetic constants for BH1657 binding to human IL-17A

| Sample | $k_{on}$ (1/Ms) | $k_{off}$ (1/s) | $K_D$ (m) |
|---|---|---|---|
| The anti-IL-17A monoclonal antibody | 3.60E+06 | 6.88E−05 | 1.91E−11 |
| BH1657 | 5.87E+06 | 6.81E−05 | 1.16E−11 |

The binding capacity of the anti-TNFα/anti-IL-17A heterodimeric antibody BH1657 to a single antigen of different species was determined by enzyme-linked immunosorbent assay (ELISA).

Detailed procedures are as follows: the recombinant human TNFα, monkey TNFα, human IL-17A or monkey IL-17A (all purchased from Sino Biological, P. R. China) was coated on wells of a 96-well high-absorption ELISA plate using a carbonate buffer solution of pH 9.6 at a coating concentration of 1 μg/mL, 100 μL per well. The coating was performed at 4° C. overnight. The plate was washed with PBST 5 times. The wells were blocked with 300 μL per well of PBST containing 1% BSA, and incubated for 1 hour at 25° C., and washed with PBST 5 times. BH1657 samples (sequentially diluted with PBST containing 1% BSA) and a control were added in an amount of 100 μL per well, and incubated at 25° C. for 1 hour. The wells were washed with PBST 5 times. Then, a horseradish peroxidase-labeled anti-human IgG antibody (Chemicon, cat #AP309P) diluted 1:10000 in PBST containing 1% BS was added in an amount of 100 μL per well, and incubated at 25° C. for 1 hour. The wells were washed with PBST 5 times. The chromogenic substrate TMB was added in an amount of 100 μL per well, and developed for 10 minutes at room temperature. Color development was terminated by adding 1M $H_2SO_4$ in an amount of 100 μL per well. The absorbance at 450 nm was read on a microplate reader.

The binding capacities of BH1657 to TNFα of different species and IL-17A of different species are shown in Table 4. The anti-TNFα/anti-IL-17A heterodimer has good binding capacities to human TNFα, monkey TNFα, human IL-17A and monkey IL-17A, and shows similar activities with the parental monoclonal antibodies.

TABLE 4

Bindings of BH1657 to human and monkey TNFα and IL-17A

| Test sample | EC$_{50}$ (nM) | | | |
|---|---|---|---|---|
| | Human TNFα | Monkey TNFα | Human IL-17A | Monkey IL-17A |
| The anti-TNFα monoclonal antibody | 0.030 | 0.025 | / | / |
| The anti-IL-17A monoclonal antibody | / | / | 0.026 | 0.029 |
| BH1657 | 0.042 | 0.034 | 0.030 | 0.033 |

Example 8. In Vitro Neutralizing Activity of the Anti-TNFα/Anti-IL-17A Heterodimeric Antibody Human prepuce fibroblast HFF-1 can secrete a series of cytokines and chemokines under the stimulation of TNFα or IL-17A, and is used for measuring the neutralizing activity of the anti-TNFα/anti-IL-17A heterodimeric antibody BH1657 to the targets thereof.

Figure 9:
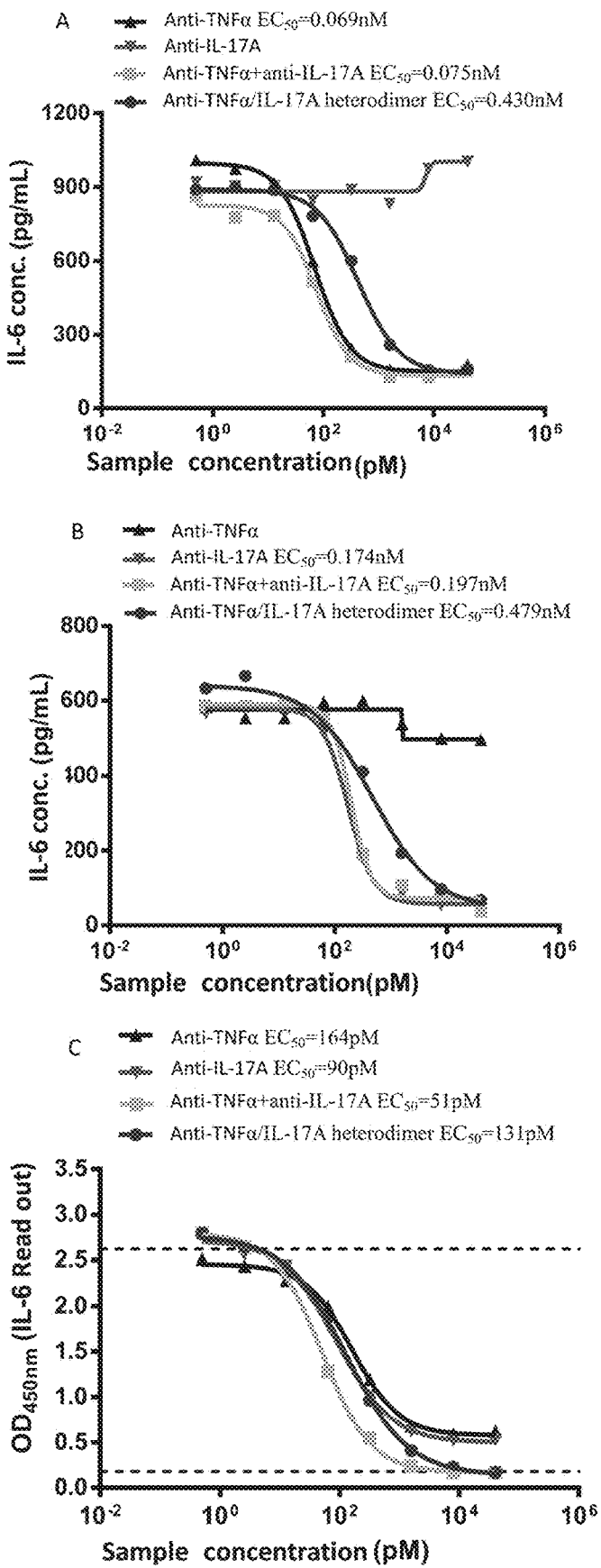
FIG. 9 shows in vitro activity of neutralizing a target antigen of the anti-TNFα/anti-IL-17A heterodimeric antibody BH1657, where A shows the activity of neutralizing TNFα of BH1657, B shows the activity of neutralizing IL-17A of BH1657, and C shows neutralizing activity of BH1657 in the presence of both TNFα and IL-17.

TNFα neutralizing activity: the BH1657 sample and the control sample were sequentially diluted in DMEM complete medium (GIBCO, cat #11995-073) containing 15% FBS (Hyclone, cat #SH 30084.03) in an amount of 50 μL per well, and added to the cell culture plate. Human TNFα at a concentration of 2 ng/mL (final concentration 0.5 ng/mL) diluted in the same complete medium was then added to the cell culture plate in an amount of 50 μL per well, and incubated for 1 hour at 37° C. in an incubator under 5% CO$_2$ atmosphere. HFF-1 cells (ATCC, cat #SCRC-1041) were then resuspended in the complete medium and seeded into wells of a 96 well cell culture plate at a density of 5000 cells per well in an amount of 100 μL per well. Cells were incubated for 24 hours at 37° C. in an incubator under 5% CO$_2$ atmosphere. After incubation, the cell culture plate was centrifuged at 250 g for 5 minutes, the culture supernatant was recovered, and the level of human IL-6 was measured by using a human IL-6 ELISA kit (R & D systems, product #S6050) according to the instructions thereof. As shown in FIG. 9A, BH1657 significantly inhibited TNFα-induced IL-6 secretion, showing good activity of neutralizing TNFα, slightly weaker than its bivalent anti-TNFα parental monoclonal antibody.

IL-17A neutralizing Activity: the BH1657 sample and the control sample were sequentially diluted in DMEM complete medium (GIBCO, cat #11995-073) containing 15% FBS (Hyclone, cat #SH 30084.03) in an amount of 50 μL per well, and added to the cell culture plate. Human IL-17A at a concentration of 20 ng/mL (final concentration 5 ng/mL) diluted in the same complete medium was then added to the cell culture plate in amount of 50 μL per well, and incubated for 1 hour at 37° C. in an incubator under 5% CO$_2$ atmosphere. HFF-1 cells were then resuspended in the complete medium and seeded into the wells of a 96 well cell culture plate at a density of 5000 cells per well in an amount of 100 μL per well. Cells were incubated for 24 hours at 37° C. in an incubator under 5% CO$_2$ atmosphere. After incubation, the cell culture plate was centrifuged at 250 g for 5 minutes, the culture supernatant was recovered, and the level of human IL-6 was measured by using a human IL-6 ELISA kit (R & D systems, product #S6050) according to the instructions thereof. As shown in FIG. 9B, BH1657 significantly inhibited IL-17A-induced IL-6 secretion, showing good activity of neutralizing IL-17A, slightly weaker than its bivalent anti-IL-17A parental monoclonal antibody.

TNFα and IL-17A have a synergistic effect on HFF-1 cells. Determination of the neutralizing activity in the presence of both TNFα and IL-17A: the BH1657 sample and the control sample were sequentially diluted in DMEM complete medium (GIBCO, cat #11995-073) containing 15% FBS (Hyclone, cat #SH30084.03) in an amount of 50 μL per well, and added to the cell culture plate. Human TNFα at a concentration of 2 ng/mL (final concentration 0.5 ng/mL) and human IL-17A at a concentration of 10 ng/mL (final concentration 2.5 ng/mL) diluted in the same complete medium were added to the wells of a cell culture plate, 50 μL per well, and incubated for 1 hour at 37° C. in an incubator under 5% CO$_2$ atmosphere. HFF-1 cells were then resuspended in the complete medium and seeded into the wells of a 96 well cell culture plate at a density of 5000 cells per well in an amount of 100 μL per well. Cells were incubated for 24 hours at 37° C. in an incubator under 5% CO$_2$ atmosphere. After incubation, the cell culture plate was centrifuged at 250 g for 5 minutes, the culture supernatant was recovered, and the level of human IL-6 was measured by using a human IL-6 ELISA kit (R & D systems, product #S6050) according to the instructions thereof. As shown in FIG. 9C, BH1657 significantly inhibited TNFα- and IL-17A-induced IL-6 secretion synergistically of HFF-1, and even exhibited complete inhibition of IL-6 at high concentrations, which was stronger than its bivalent parental monoclonal antibody.

Figure 10:
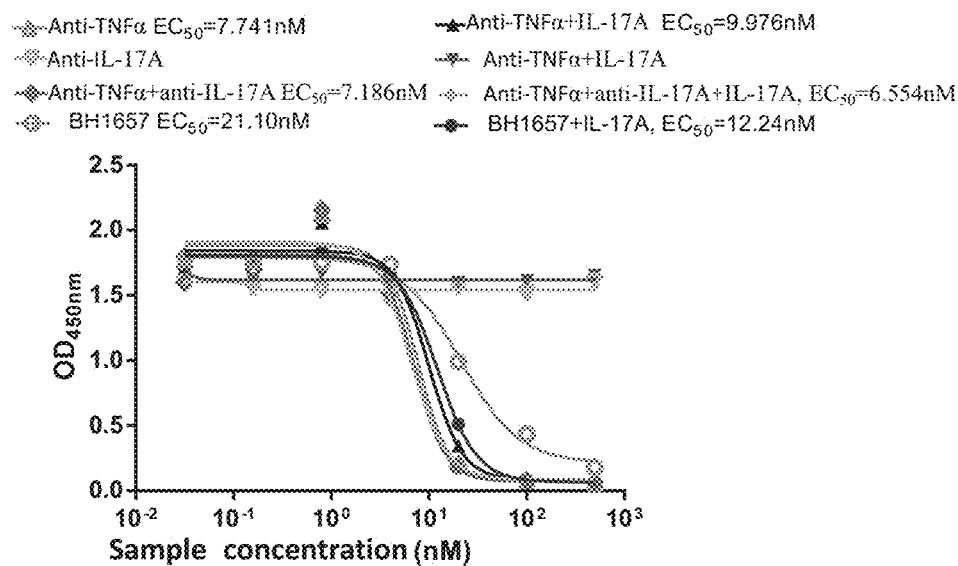
FIG. 10 shows that anti-TNFα activity of the anti-TNFα/anti-IL-17A heterodimeric antibody BH1657 is affected by the presence or absence of IL-17A, wherein A shows effect of IL-17A on blocking TNFα/TNFR2 activity of BH1657 and B shows effect of IL-17A on activity of neutralizing TNFα of BH1657.
Figure 10:
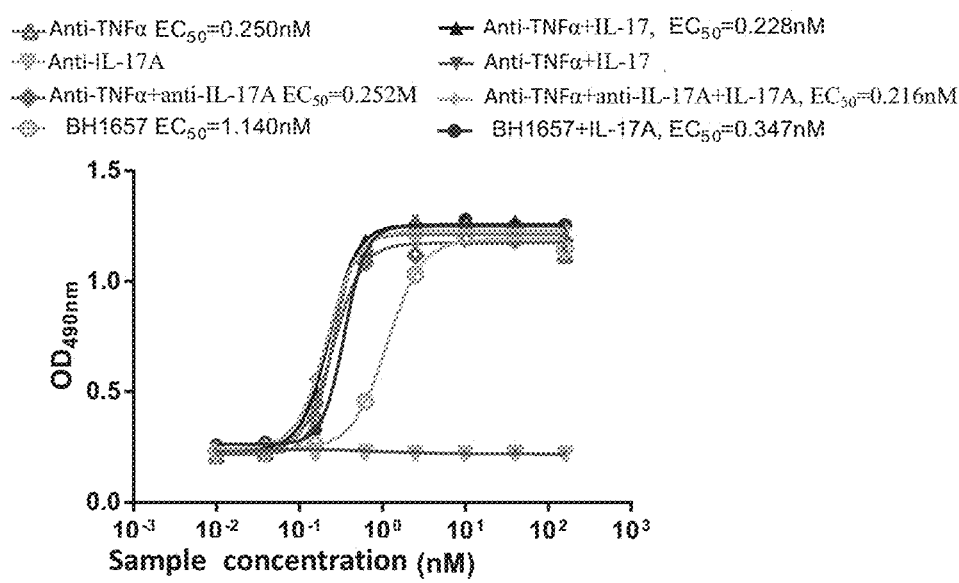

Example 9. The Anti-TNFα Activity of the Anti-TNFα/Anti-IL-17A Heterodimeric Antibody Depends on the Presence or Absence of IL-17A The effects of IL-17A on TNFα/TNFR2 blocking activity of the anti-TNFα/IL-17A heterodimeric antibody BH1657 were determined by ELISA. Detailed procedures are as follows: the recombinant human TNFα (purchased from Sino Biological, P.R. China) was coated on wells of a 96-well high-adsorption ELISA plate using a carbonate buffer solution of pH 9.6 at a coating concentration of 1 μg/mL and in a coating amount of 100 μL per well. The coating was performed at 4° C. overnight. The wells were washed with PBST 5 times. The wells were blocked with 300 μL per well of PBST containing 1% BSA, and incubated for 1 hour at 25° C., and washed with PBST 5 times. BH1657 samples (sequentially diluted with PBST containing 1% BSA) and a control 25 μL, human IL-17A (purchased from Sino Biological, P. R. China) 25 μL (16 μL/mL, final concentration 4 μg/mL), biotin-labeled TNFR2-Fc (purchased from Sino Biological, P. R. China) 50 μL (0.3 μg/mL, final concentration 0.15 μg/mL) were added and incubated at 25° C. for 1 hour. The wells were washed with PBST 5 times. Then, horseradish peroxidase-labeled streptavidin (BD, cat #554066) 1:1000 diluted in PBST containing 1% BSA was added in an amount of 100 μL per well, and incubated at 25° C. for 1 hour. The wells were washed with PBST 5 times. The chromogenic substrate TMB was added in an amount of 100 μL per well, and color developed at room temperature for 10 minutes. Color development was terminated by adding 1M H$_2$SO$_4$ in an amount of 100 μL per well. The absorbance at 450 nm was read on a microplate reader. As shown in FIG. 10A, in the absence of IL-17A, TNFα/TNFR2 blocking activity was reduced as compared to the parental monoclonal antibody; in the presence of IL-17A, said activity was enhanced, comparable to that of the parental monoclonal antibody. The TNFα/TNFR2 blocking activity of the anti-TNFα parental monoclonal antibody was not affected by IL-17A.

The effect of IL-17A on TNFα neutralizing activity of the anti-TNFα/anti-IL-17A heterodimeric antibody BH1657 was determined using L-929 cells (purchased from the Basic Medical Cell Center, the Institute of Basic Medical Sciences, Chinese Academy of Medical Sciences). Detailed procedures are as follows: the complete medium for L-929 cells was MEM (GIBCO, cat #10370-021) medium containing 10% FBS (Hyclone, cat #SH 30084.03). L-929 cells were resuspended in the complete medium and plated in the wells of a 96 well cell culture plate at a density of 15000 cells per well in an amount of 100 μL per well. Cells were incubated overnight at 37° C. in an incubator under 5% $CO_2$ atmosphere. The culture supernatant was discarded and the BH1657 sample and the control sample were sequentially diluted in the complete medium containing 2 ng/mL human TNFα and 1 μg/mL actinomycin D, 100 μL per well, and added to the wells of a cell culture plate. Cells were incubated for further 24 hours at 37° C. in an incubator under 5% $CO_2$ atmosphere. At the end of the incubation, 20 μL of MTS (CellTiter 96 Aqueous One Solution, Promega, cat #G358B) was added to each well of the cell culture plate to measure cell viability. Results are shown in FIG. 10B. The TNFα neutralizing activity of the anti-TNFα portion of the anti-TNFα/anti-IL-17A heterodimeric bispecific antibody was significantly enhanced in the presence of IL-17A as compared to the absence of IL-17A. This difference in activity of the anti-TNFα/anti-IL-17A bispecific antibody suggests that it has stronger TNFα neutralizing activity at the focal site of high IL-17A levels, while it shows weaker TNFα neutralizing activity in the circulatory system of low IL-17A levels, thereby indicating that the bispecific antibody can effectively treat diseases while maintaining lower toxic and side effects.

Example 10. In Vivo Neutralizing Activity of the Anti-TNFα/Anti-IL-17A Heterodimeric Antibody 6-8 week-old female BALB/c mice purchased from Beijing HFK Bioscience, Co., Ltd. were used as experimental materials. One week after the mice were acclimatized to the environment, they were randomized into groups, each group containing 6 mice. Each group was administered with the anti-TNFα/IL-17A heterodimeric antibody BH1657, the anti-TNFα monoclonal antibody, the anti-IL-17A monoclonal antibody, and a combination of the anti-TNFα monoclonal antibody and the anti-IL-17A monoclonal antibody at three dose levels (0.1 mg/kg, 1 mg/kg, 10 mg/kg for monoclonal antibodies, 0.2 mg/kg, 2 mg/kg, 20 mg/kg for the bispecific antibody) respectively, via intravenous injection, in a single dose. One hour after administration, human TNFα and IL-17A were injected subcutaneously, 0.2 μg TNFα and 20 μg IL-17A per mouse. After 2 hours, blood was collected from orbit without anticoagulation, and blood sample was allowed to stand at room temperature for 30 minutes to 1 hour. After clotting, the blood sample was centrifuged at 3000 rpm for 10 minutes to obtain a serum sample. The concentration of mouse CXCL1 in serum was determined using a mouse CXCL1 ELISA kit (RayBiotech, cat #ELM-KC) according to the instructions thereof.

Figure 11:
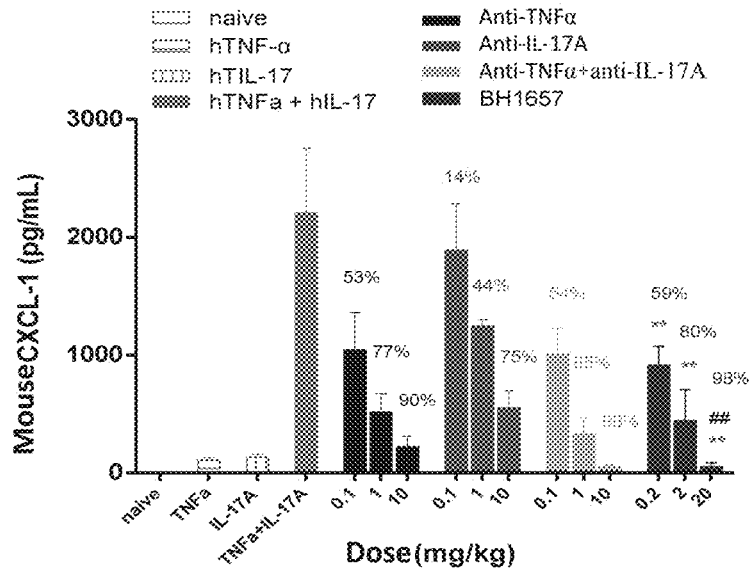
FIG. 11 shows hi vivo activity of neutralizing a target antigen of the anti-TNFα/anti-IL-17A heterodimeric antibody BH1657. ##$p<0.01$ vs anti-TNFα; **$p<0.01$ vs anti-IL-17A.

As shown in FIG. 11, BH1657 significantly inhibited TNFα- and IL-17A-stimulated CXCL1 secretion in mouse synergistically, and even exhibited complete inhibition of CXCL1 at high concentrations, which was stronger than those of its bivalent parental monoclonal antibody.

Example 11. Target Binding Activities of the Anti-Mouse TNFα/Anti-Mouse IL-17A Heterodimeric Antibody The binding capacities of the anti-mouse TNFα/anti-mouse IL-17A heterodimeric antibody (i.e., BH1654) to a single antigen of different species were determined by an enzyme-linked immunosorbent assay (ELISA). Detailed procedures are as follows: the recombinant mouse TNFα, rat TNFα, mouse IL-17A and rat IL-17A (all purchased from Sino Biological, P. R. China) were coated on wells of a 96-well high-adsorption ELISA plate using a carbonate buffer solution of pH 9.6 at a coating concentration of 1 μg/mL and in a coating amount of 100 μL per well. The coating was performed at 4° C. overnight. The wells were washed with PBST 5 times. The wells were blocked with 300 μL per well of PBST containing 1% BSA, and incubated for 1 hour at 25° C., and washed with PBST 5 times. BH1654 samples (sequentially diluted with PBST containing 1% BSA) and controls (the anti-mouse TNFα mAb and the anti-mouse IL-17A mAb) were added in an amount of 100 μL per well, and incubated at 25° C. for 1 hour. The wells were washed with PBST 5 times. Then, horseradish peroxidase-labeled anti-human IgG antibody (Chemicon, cat #AP 309P) 1:10000 diluted in PBST containing 1% BSA was added in an amount of 100 μL per well, and incubated at 25° C. for 1 hour. The wells were washed with PBST 5 times. The chromogenic substrate TMB was added in an amount of 100 μL per well, and color developed at room temperature for 10 minutes. Color development was terminated by adding 1M $H_2SO_4$ in an amount of 100 μL per well. The absorbance at 450 nm was read on a microplate reader.

The binding capacities of BH1654 to TNFα of different species and IL-17A of different species are shown in Table 5. The anti-mouse TNFα/anti-mouse IL-17A heterodimer has good mouse TNFα and mouse IL-17A binding force, and has similar activities to those of the parental monoclonal antibodies. It does not bind to rat TNFα and weakly binds to rat IL-17A.

TABLE 5

Binding of BH1654 to mouse and rat TNFα and IL-17A

| Sample | $EC_{50}$ (nM) | | | |
| --- | --- | --- | --- | --- |
|  | Mouse TNFα | Rat TNFα | Mouse IL-17A | Rat IL-17A |
| The anti-mouse TNFα monoclonal antibody | 0.025 | / | / | / |
| The anti-mouse IL-17A monoclonal antibody | / | / | 0.027 | 0.032 |
| BH1654 | 0.040 | / | 0.032 | 0.311 |

Example 12. Pharmacodynamic Studies of the Anti-Mouse TNFα/Anti-Mouse IL-17A Heterodimeric Antibody in the Type II Collagen-Induced Mouse Arthritis (mCIA) Model Mouse CIA model can better simulate the human rheumatoid diseases and predict the curative effect of the medicament on the human rheumatoid diseases, and is widely applied to the research of the pathogenesis of the rheumatoid arthritis and the screening of the therapeutic medicaments. 8-week-old male DBA1/J mice (purchased from Shanghai SLAC Laboratory Animal Co., Ltd) were selected as the experimental animals. The mice were adapted to the environment for a week. Thereafter, 5 mice were randomly selected as naive control mice, and the rest were used for establishing a mouse CIA model. CIA model was obtained after primary & booster immunizations. Primary immunization was performed by injecting intradermally into the tail root of the mouse an emulsion formed of 70 μg of bovine collagen type II (Chondrex, cat #20022) mixed with Freund's complete adjuvant (Sigma-Aldrich, cat #F5881). Three weeks later, booster immunization was performed. Booster immunization was performed by injecting intradermally into the back of the mouse an emulsion formed of 70 μg of bovine collagen type II mixed with Freund's incomplete adjuvant (Sigma-Aldrich, cat #F5506). After the booster immunization, mice were grouped (8 mice in each group) after clinical arthritis symptoms such as redness and edema of limbs, feet and claws of mice were observed.

Each group of CIA model mice were administered separately with the following agents respectively: drug vehicle (PBS), the anti-mouse TNFα monoclonal antibody (70 nmol/kg), the anti-mouse IL-17A monoclonal antibody (70 nmol/kg), a combination of the anti-mouse TNFα monoclonal antibody and the anti-mouse IL-17A monoclonal antibody (70 nmol/kg+70 nmol/kg), and the anti-mouse TNFα/anti-mouse IL-17A heterodimeric antibody BH1654 (70 nmol/kg, 140 nmol/kg), once every other day via intraperitoneal injection, 7 times in total. After administration, the body weight was weighed once every other day, pathological changes of the four paws were observed, and the severity of arthritis was scored: 0=no evidence of redness and edema, 1=erythema and mild edema confined to ankle joint or tarsal joint, 2=erythema and mild edema from the ankle joint to the tarsal joint, 3=erythema and moderate edema from the ankle joint to the metatarsal joint, 4=erythema and severe edema from the ankle to paws including phalangeal joint, or ankylosis of four limbs. Inflammation scores were given to all limbs of mice, and the maximum score for each mouse was 16 scores.

Figure 12:
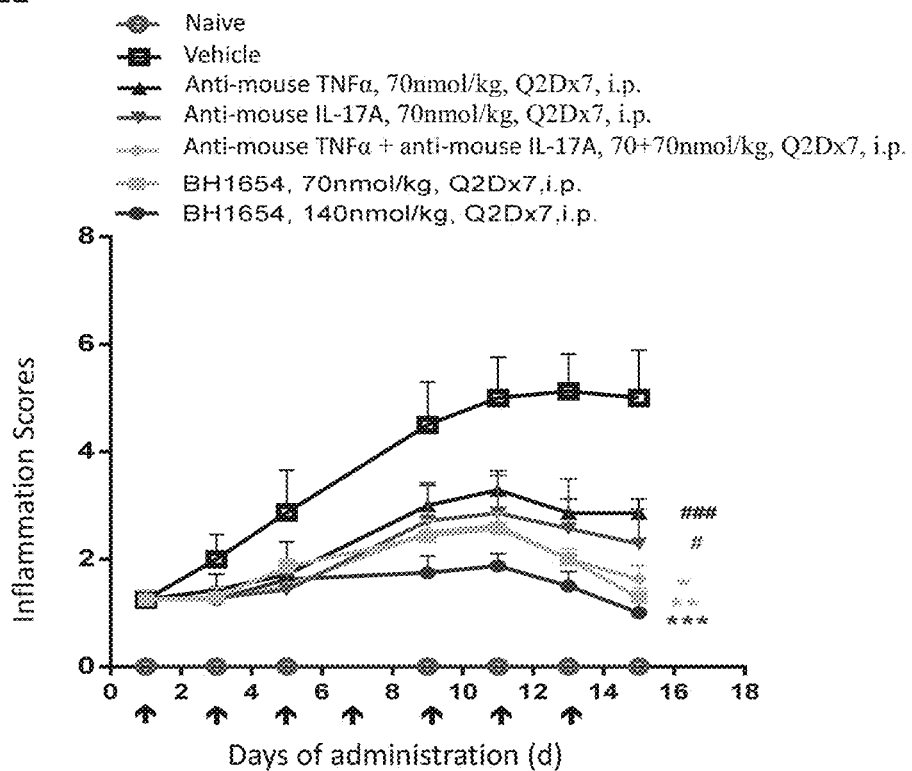
FIG. 12 shows efficacy of the anti-mouse TNFα/anti-mouse IL-17A heterodimeric antibody BH1654 in type II collagen-induced mouse arthritis (mCIA) model. *$p<0.5$, $p<0.01$, * $p<0.001$ vs vehicle; #$p<0.05$, #$p<0.001$ vs BH1654 140 nmol/kg.

As shown in FIG. 12, mice from the naive control group produced no inflammatory response, significant inflammatory response was found in CIA model mice in the vehicle group, with a rapid increase in the arthritis index. The arthritis scores of mice from the CIA model mice of the administration group of the anti-mouse TNFα/anti-mouse IL-17A heterodimeric antibody BH1654 was significantly inhibited, showing a better inflammation alleviation effect than the anti-mouse TNFα monoclonal antibody and the anti-mouse IL-17A monoclonal antibody.

Example 13. Pharmacodynamic Studies of the Anti-Mouse TNFα/Anti-Mouse IL-17A Heterodimeric Antibody in the Glucose-6-Phosphate Isomerase-Induced Mouse Arthritis (mGPI) Model Mouse GPI model was established by immunizing mice with Glucose-6-phosphate isomerase (GPI) or its 325-339 peptide fragment ($GPI_{325-339}$). This model, an animal model developed in recent years, can better simulate human rheumatoid diseases, and is suitable for the research of the pathogenesis of the rheumatoid arthritis and the screening of the therapeutic medicaments. 8-week-old male DBA1/J mice (purchased from Shanghai SLAC Laboratory Animal Co., Ltd) were selected as the experimental animals. The mice were adapted to the environment for a week. Thereafter, 5 mice were randomly selected as naive control mice, and the rest were used for establishing a mouse GPI model. GPI model was obtained via one shot immunization. Immunization was performed by injecting intradermally into the tail root of the mouse an emulsion formed of 100 μg of $GPI_{325-339}$ (synthesized by chemistry group of BEIJING HANMI PHARMACEUTICAL CO., amino acid sequence IWYINCFGCETHAML (SEQ ID NO: 19)) mixed with Freund's complete adjuvant (Sigma-Aldrich, cat #F5881). Pertussis toxin (Merck, cat #516560) was injected intraperitoneally on day 1 (the day of immunization) and day 3 of immunization. On day 5 after immunization, mice were randomly grouped, 8 mice in each group.

Each group of GPI model mice were administered prophylactically with the following agents respectively: drug vehicle (PBS), the anti-mouse TNFα monoclonal antibody (35 nmol/kg), the anti-mouse IL-17A monoclonal antibody (35 nmol/kg), a combination of the anti-mouse TNFα monoclonal antibody and the anti-mouse IL-17A monoclonal antibody (35 nmol/kg+35 nmol/kg), and the anti-mouse TNFα/anti-mouse IL-17A heterodimer antibody BH1654 (35 nmol/kg, 70 nmol/kg), once every other day via intraperitoneal injection, 7 times in total. After administration, the body weight was weighed once a day, pathological changes of the four paws were observed, and the severity of arthritis was scored: 0=no evidence of redness and edema, 1=erythema and mild edema confined to ankle joint or tarsal joint, 2=erythema and mild edema from the ankle joint to the tarsal joint, 3=erythema and moderate edema from the ankle joint to the metatarsal joint, 4=erythema and severe edema from the ankle to paws including phalangeal joint, or ankylosis of four limbs. Inflammation scores were given to all limbs of mice, and the maximum score for each mouse was 16 scores.

Figure 13:
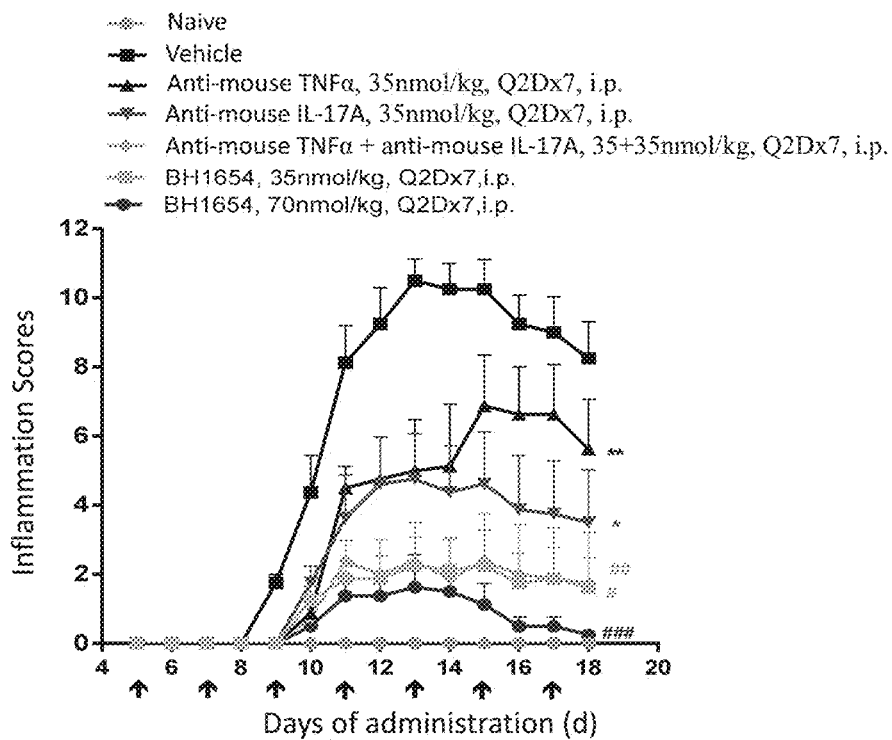
FIG. 13. shows the efficacy of the anti-mouse TNFα/anti-mouse IL-17A heterodimeric antibody BH1654 in a glucose-6-phosphate isomerase-induced mouse arthritis (mGPI) model. #$p<0.5$, #$p<0.01$, #$p<0.001$ vs vehicle; *$p<0.05$, **$p<0.01$, vs BH1654, 70 nmol/kg.

As shown in FIG. 13, mice from the naive control group produced no inflammatory response, significant inflammatory response was found in GPI model mice in the vehicle group, and the anti-mouse TNFα/anti-mouse IL-17A heterodimeric antibody BH1654 showed good anti-inflammatory effects at 35 nmol/kg and 70 nmol/kg, and had dose-dependency. The inflammation relieving effect of BH1654 is stronger than that of the anti-mouse TNFα monoclonal antibody and the anti-mouse IL-17A monoclonal antibody.

Example 14. Pharmacodynamic Studies of the Anti-Mouse TNFα/Anti-Mouse Il-17A Heterodimeric Antibody in the Zymosan-Induced SKG Mouse Psoriatic Arthritis (PsA) Model Mouse psoriatic arthritis model was established by immunizing SKG mice with zymosan (a glucan). The model, an animal model developed in recent years, simulates human spondyloarthitis (a kind of immune diseases, including ankylosing spondylitis, psoriatic arthritis and the like). This example used this model for the evaluation of therapeutic medicaments for psoriatic arthritis. 9 to 10-week-old female SKG/Jcl mice (purchased from CLEA, Japan) were selected as the experimental animals. The mice were adapted to the environment for a week. Thereafter, 4 mice were randomly selected as naive control mice and the rest was used for establishing the mouse PsA model. PsA model was obtained via one shot immunization. Immunization was performed by injecting intraperitoneally into mice 3 mg zymosan (purchased from Sigma-Alrich, cat #Z4250) in a PBS buffer. On day 12 after immunization, mice were randomly grouped, 8 mice in each group.

Each group of PsA model mice were administered prophylactically with the following agents respectively: drug vehicle (PBS), the anti-mouse TNFα monoclonal antibody (35 nmol/kg), the anti-mouse IL-17A monoclonal antibody (35 nmol/kg), the anti-mouse TNFα/anti-mouse IL-17A heterodimer antibody BH1654 (70 nmol/kg), twice every week via intraperitoneal injection, 8 times in total. After administration, the body weight was weighed twice a week, pathological changes of the four paws were observed, and the severity of arthritis was scored: 0=no abnormal phenomena such as joint or toe swelling. 0.1=red and swollen toes, 0.1 for one toe. 0.5=slight swelling of the ankle joint, the first onset occurred on the lateral side of the ankle joint. 1=apparent swelling of the ankle joint. 1.5=a score of degree, apparent swelling of the ankle joint and a trend of spreading to toes, and the swelling degree was apparently greater than 1 and less than 2. 2=moderate swelling of the ankle joint, swelling keeps spreading to toes but not to the toe joints. 2.5=a score of degree, swelling degree was significantly greater than 2, but not to the toe joints. 3=severe swelling from ankle to toes. The highest severe swelling of the joints was scored as 3, which is generally accompanied by severe toe swelling. This scoring system evaluates joint swelling and toe swelling separately, with joint swelling superimposed by a swelling degree of 0.5 point, and toes scored 0.1 point per toe. Score was marked by joint score+toe score.

Figure 14:
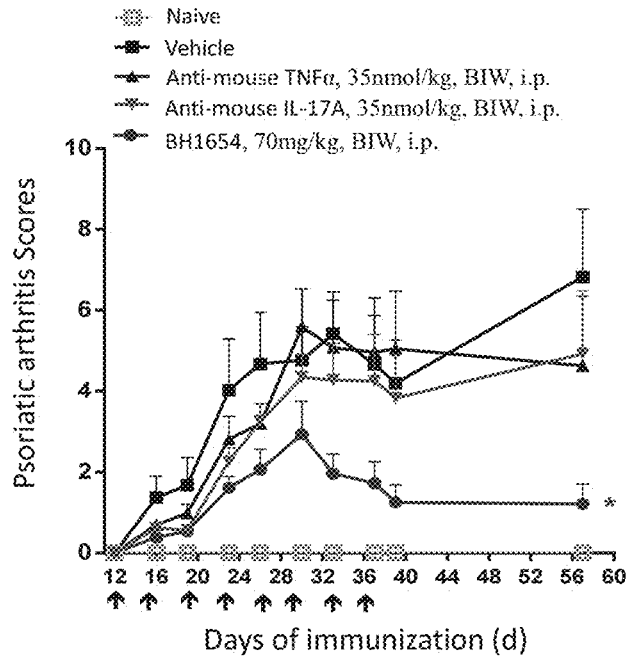
FIG. 14. shows the efficacy of the anti-mouse TNFα/anti-mouse IL-17A heterodimeric antibody BH1654 in the zymosan-induced SKG mouse psoriatic arthritis (PsA) model. #$p<0.5$ vs vehicle.

As shown in FIG. 14, mice from the naive control group produced no inflammatory response, significant inflammatory response was found in PsA model mice in the solvent group, with psoriasis and psoriatic arthritis symptoms, and the anti-mouse TNFα/anti-mouse IL-17A heterodimeric antibody BH1654 showed good anti-inflammatory effects at 70 nmol/kg, while the anti-mouse TNFα monoclonal antibody and the anti-mouse IL-17A monoclonal antibody substantially had no anti-inflammatory effect in this model.

Example 15. Apoptosis-Inducing Effects of the Anti-TNFα/Anti-IL-17A Heterodimeric Antibody on the Transmembrane TNFα-Expressing Cells Apoptosis of immune cells expressing the transmembrane TNFα can be induced by an outside-to-inside signaling mediated by the transmembrane TNFα after binding of the TNFα antagonist to the transmembrane TNFα, and this apoptosis is associated with the decreased host defense caused by the TNFα antagonist. The apoptosis-inducing effect of Humira® is stronger than that of Enbrel®, and the infection risk after administration of Humira® is also higher than that of Enbrel®. This example relates to the detection of the apoptosis-inducing effect of the anti-TNFα/anti-IL-17A heterodimeric antibody BH1657. The specific implementation process is as follows: in accordance with a reference (Arthritis & Rheumatism, 2008, 58(5): 1248-1257), a cell line expressing the transmembrane TNFalpha was constructed on Jurkat cells (purchased from Basic Medical Cell Center, the Institute of Basic Medical Sciences, Chinese Academy of Medical Sciences) and named as Jurkat/tmTNFα, and cultured in RPMI 1640 medium (GIBCO, cat #22400-089) containing 10% FBS (Hyclone, cat #SH30084.03). On the day of the experiment, Jurkat/tmTNFα cells in exponential phase were collected, resuspended in RPMI 1640 medium containing 2% FBS, and seeded into wells of a 12-well cell culture plate, 400000 cells per well, 1 mL per well. The samples to be tested were sequentially diluted in RPMI 1640 medium containing 2% FBS and added to wells of a 12-well cell culture plate, 1 mL per well. After 24 hours of co-incubation, cells were collected and stained with an apoptosis test kit (Sigma-Alrich, cat #APOAF-50TST) according to the kit instructions. The cells were then analyzed for apoptosis by a flow cytometry.

As shown in Table 6, the data indicated that Humira® induced a stronger apoptotic effect on Jurkat/tmTNFα cells, probably because the anti-TNFα of Humira® is bivalent and able to cross-link different transmembrane TNFαs, inducing a stronger outside-to-inside apoptotic signalling. However, the anti-TNFα of the anti-TNFα/anti-IL-17A heterodimeric antibody BH1657 is monovalent, and the apoptosis-inducing effect is weaker and comparable to that of Enbrel®. It is therefore speculated that as comparing with Humira®, the anti-TNFα/anti-IL-17A heterodimeric antibodies may have a lower inhibitory effect on host resistance, and thus may have a lower risk of infection.

TABLE 6

Apoptosis-inducing effects of BH1657 on Jurkat/tmTNFα cells

| Sample | Apoptosis ratio (%) |
| --- | --- |
| Solvent | 15.48 |
| Humira ®, 1 µg/mL | 29.86 ± 1.30 |
| Humira ®, 10 µg/mL | 28.19 ± 0.08 |
| Enbrel ®, 1 µg/mL | 18.97 ± 0.60 |
| Enbrel ®, 10 µg/mL | 20.98 ± 0.27 |
| Anti-IL-17A monoclonal antibody, 1 µg/mL | 14.90 ± 0.12 |
| Anti-IL-17A monoclonal antibody, 10 µg/mL | 16.09 ± 0.21 |
| Humira ® + anti-IL-17A monoclonal antibody, 1 + 1 µg/mL | 28.69 ± 0.04 |
| Humira ® + anti-IL-17A monoclonal antibody, 10 + 10 µg/mL | 26.50 ± 0.70 |
| BH1657, 1 µg/mL | 18.49 ± 0.45 |
| BH1657, 2 µg/mL | 18.65 ± 1.52 |
| BH1657, 10 µg/mL | 17.60 ± 003 |
| BH1657, 20 µg/mL | 17.77 ± 0.93 |

The invention claimed is:

1. A heterodimeric bispecific antibody comprising a first Fc chain and a second Fc chain, and a first antigen-binding functional region capable of specifically binding to TNFα and a second antigen-binding functional region capable of specifically binding to IL-17A;
    wherein both the first Fc chain and the second Fc chain are Fc fragments of an immunoglobulin G comprising amino acid substitutions and together form a heterodimer that can bind to an Fc receptor;
    wherein the first Fc chain and the second Fc chain are linked to the first and second antigen-binding functional regions, respectively, via a covalent bond or a linker; and
    wherein either the first Fc chain or the second Fc chain has amino acid substitutions of T366L and D399R, and the other chain has amino acid substitutions of L351E, Y407L, and K409V,
    wherein the first antigen-binding functional region comprises the amino acid sequences of SEQ ID NOs: 2 and 6, and the second antigen-binding functional region comprises the amino acid sequences of SEQ ID NOs: 10 and 12, and
    wherein the amino acid positions are numbered according to the Kabat EU index numbering system.

2. The heterodimeric bispecific antibody of claim 1, wherein both the first antigen-binding functional region and the second antigen-binding functional region are selected from the group consisting of a Fab fragment, a scFv fragment, a variable domain fragment Fv and a heavy chain variable region fragment VHH of a heavy chain antibody.

3. The heterodimeric bispecific antibody of claim 1, wherein both the first antigen-binding functional region and the second antigen-binding functional region are Fab fragments.

4. The heterodimeric bispecific antibody of claim 1, wherein one of the first antigen-binding functional region and the second antigen-binding functional region is a Fab fragment and the other is a scFv fragment.

5. The heterodimeric bispecific antibody of claim 3, wherein the Fab fragments comprise a first heavy chain variable region and a second heavy chain variable region that are different from each other, and a first light chain variable region and a second light chain variable region that are different from each other.

6. The heterodimeric bispecific antibody of claim 1, wherein when each of the first Fc chain covalently bonded to the TNFα antigen binding region and the second Fc chain covalently bonded to the IL-17A antigen binding region, or each of the first Fc chain covalently bonded to the IL-17A antigen binding region and the second Fc chain covalently bonded to the TNFα antigen binding region, is present alone in the presence of a reducing agent, the weight ratio of the constituent homodimers are less than 50%.

7. An isolated polynucleotide, encoding the heterodimeric bispecific antibody of claim 1.

8. The isolated polynucleotide of claim 7, wherein a nucleotide sequence of the isolated polynucleotide is selected from the group consisting of: SEQ ID NOs: 1, 3, 5, 7, 9, 11, and 13.

9. A recombinant expression vector, comprising the isolated polynucleotide of claim 7.

10. The recombinant expression vector of claim 9, wherein the recombinant expression vector is a plasmid vector X0GC modified based on pcDNA.

11. A host cell, comprising the isolated polynucleotide of claim 7.

12. The host cell of claim 11, selected from the group consisting of a human embryonic kidney cell HEK293 cell, or a HEK293T cell, a HEK293E cell and a HEK293F cell derived from a HEK293 cell; a hamster ovary cell CHO cell, or a CHO-S cell, a CHO-dhfr-cell, a CHO/DG 44 cell and a ExpiCHO cell derived from a CHO cell.

13. A composition, comprising the heterodimeric bispecific antibody of claim 1, and a pharmaceutically acceptable carrier.

14. A method of producing the heterodimeric bispecific antibody of claim 1, comprising the steps of:
    1) expressing the isolated polynucleotide of claim 7 in a host cell;
    2) reducing each protein expressed in the host cell respectively; and
    3) mixing the reduced proteins and then oxidizing the mixture.

15. The method of claim 14, wherein the host cell is selected from the group consisting of a human embryonic kidney cell HEK293 cell, or a HEK293T cell, a HEK293E cell and a HEK293F cell derived from a HEK293 cell; a hamster ovary cell CHO cell, or a CHO-S cell, a CHO-dhfr-cell, a CHO/DG 44 cell and a ExpiCHO cell derived from a CHO cell.

16. The method of claim 14, wherein the reducing step comprises: 1) performing a reduction using the reducing agent comprising 2-mercaptoethylamine, dithiothreitol, tris (2-carboxyethyl) phosphine, or a chemical derivative or combination thereof; and 2) removing the reducing agent.

17. The method of claim 14, wherein the oxidizing step is performed in air and comprises oxidation performed in the presence of an oxidizing agent selected from the group consisting of L-dehydroascorbic acid and another chemical derivative thereof.

18. The method of claim 14, which further comprises a step of isolation and purification.

19. A method of preventing and/or treating a disease, comprising a step of administering the heterodimeric bispecific antibody of claim 1 to a subject in need thereof.

20. The method of claim 19, wherein the subject is a mammal, preferably a human.

21. The method of claim 19, wherein the disease is selected from the group consisting of rheumatoid arthritis, osteoarthritis, psoriatic arthritis, ankylosing spondylitis, gouty arthritis, juvenile rheumatoid arthritis, suppurative arthritis, psoriasis, type I diabetes, multiple sclerosis, autoimmune encephalomyelitis, Crohn's disease, systemic vasculitis, dermatomyositis, mixed connective tissue disease, lupus erythematosus, idiopathic thrombocytopenia purpura, primary Sjogren's syndrome, glomerulonephritis, gout, organ-transplant rejection, asthma or atherosclerosis.

22. The heterodimeric bispecific antibody of claim 1, wherein the first antigen-binding functional region comprises the amino acid sequences of SEQ ID NOs: 4 and 8.

23. The heterodimeric bispecific antibody of claim 1, wherein the second antigen-binding functional region comprises the amino acid sequences of SEQ ID NOs: 4 and 14.

* * * * *